US008728002B2

(12) United States Patent
Al-Rawas et al.

(10) Patent No.: US 8,728,002 B2
(45) Date of Patent: May 20, 2014

(54) SYSTEM AND METHOD FOR ASSESSING REAL TIME PULMONARY MECHANICS

(75) Inventors: Nawar Nazar Yousif Al-Rawas, Gainesville, FL (US); Andrea Gabrielli, Gainesville, FL (US); Neil Russell Euliano, Gainesville, FL (US); Michael Joseph Banner, Alachua, FL (US)

(73) Assignees: University of Florida Research Foundation, Inc., Gainesville, FL (US); Convergent Engineering, Inc., Newberry, FL (US)

( * ) Notice: Subject to any disclaimer, the term of this patent is extended or adjusted under 35 U.S.C. 154(b) by 2 days.

(21) Appl. No.: 13/260,467

(22) PCT Filed: Dec. 28, 2010

(86) PCT No.: PCT/US2010/062232
§ 371 (c)(1),
(2), (4) Date: Oct. 26, 2011

(87) PCT Pub. No.: WO2011/090716
PCT Pub. Date: Jul. 28, 2011

(65) Prior Publication Data
US 2012/0330177 A1    Dec. 27, 2012

Related U.S. Application Data

(60) Provisional application No. 61/290,392, filed on Dec. 28, 2009, provisional application No. 61/309,979, filed on Mar. 3, 2010.

(51) Int. Cl.
*A61B 5/08*    (2006.01)

(52) U.S. Cl.
USPC .......................................... 600/533; 128/204

(58) Field of Classification Search
USPC ..................................... 600/533; 128/204.23
See application file for complete search history.

(56) References Cited

U.S. PATENT DOCUMENTS

| 7,566,310 | B2 | 7/2009 | Badr et al. |
| 2003/0010339 | A1* | 1/2003 | Banner et al. ............ 128/204.18 |
| 2007/0185406 | A1 | 8/2007 | Goldman |
| 2009/0272382 | A1 | 11/2009 | Euliano et al. |

OTHER PUBLICATIONS

Al-Rawas, N. et al., "Real-Time Calculation of Respiratory System Compliance (CRS) and Plateau Pressure (PPLT) During Pressure Support Ventilation (PSV)," *American Journal of Respiratory and Critical Care Medicine*, Poster: Mechanical Ventilation—Thematic Poster Session, 2011, vol. 193, A1693.

(Continued)

*Primary Examiner* — Michael Kahelin
*Assistant Examiner* — Mitchell Alter
(74) *Attorney, Agent, or Firm* — Saliwanchik, Lloyd & Eisenschenk

(57) ABSTRACT

A system and method of calculating an accurate estimate of pulmonary mechanics of a patient, including but not limited to compliance, resistance, and plateau pressure without modification of ventilator flow pattern. The accurate estimation of pulmonary mechanics is derived from airway pressure and flow sensors attached to the patient using novel mathematical models. These estimated figures for pulmonary mechanics (respiratory system compliance and resistance) are important for monitoring patient treatment efficacy during mechanical ventilation and ensuring alveoli do not over distend to avoid baro- and/or volutrauma, especially in patients with restrictive lung diseases. The subject method of calculating these accurate estimated figures for pulmonary mechanics is based on linear or non-linear calculations using multiple parameters derived from the above-mentioned sensors.

18 Claims, 19 Drawing Sheets

(56) References Cited

OTHER PUBLICATIONS

Al-Rawas, N. et al., "Real-Time Measurements of Inspiratory Plateau Pressure (PPLT), Respiratory System Compliance (CRS), and Resistance (RRS) During Ventilatory Support," *Critical Care Medicine*, Poster: Pulmonary—Mechanical Ventilation—1, 2010, vol. 38, No. 12, A344.

Brunner, JX et al., "Simple method to measure total expiratory time constant based on the passive expiratory flow volume curve," *Critical Care Medicine* 1995, vol. 23, pp. 1117-1122.

Guerin, C. et al., Effect of PEEP on work of breathing in mechanically ventilated COPD patients, *Intensive Care Medicine*, 2000, vol. 26, No. 9, pp. 1207-1214.

Guttmann, J. et al., "Time constant/volume relationship of passive expiration in mechanically ventilated ARDS patients," *European Respiratory Journal*, 1995, vol. 8, pp. 114-120.

Lourens M.S. et al., "Expiratory time constants in mechanically ventilated patients with and without COPD," *Intensive Care Medicine*, 2000, vol. 26, No. 11, pp. 1612-1618.

NIH NHLBI ARDS Clinical Network Mechanical Ventilation Protocol Summary, Jul. 2008, http://www.ardsnet.org/node/77791.

* cited by examiner

SUMMARY OUTPUT

| Regression Statistics | |
|---|---|
| Multiple R | 0.99590796 |
| R Square | 0.99183676 |
| Adjusted R Square | 0.991820033 |
| Standard Error | 0.68657041 |
| Observations | 648 |

ANOVA

| | df | SS | MS | F | Significance F |
|---|---|---|---|---|---|
| Regression | 1 | 3698.023834 | 3698.023834 | 7849.6759 | 0 |
| Residual | 646 | 304.516695 | 0.471388033 | | |
| Total | 647 | 3728.475501 | | | |

| | Coefficients | Standard Error | t Stat | P-value | Lower 95% | Upper 95% | Lower 95.0% | Upper 95.0% |
|---|---|---|---|---|---|---|---|---|
| Intercept | -0.135024587 | 0.082023182 | -1.646175911 | 0.100213928 | -0.296088832 | 0.026039658 | -0.296088832 | 0.026039658 |
| X Variable 1 | 1.006204074 | 0.003592448 | 280.0886925 | 0 | 0.999149789 | 1.01325836 | 0.999149789 | 1.01325836 |

FIG. 6A

| SUMMARY OUTPUT | | | | | | | | |
|---|---|---|---|---|---|---|---|---|
| *Regression Statistics* | | | | | | | | |
| Multiple R | 0.985680822 | | | | | | | |
| R Square | 0.971566683 | | | | | | | |
| Adjusted R Square | 0.971522668 | | | | | | | |
| Standard Error | 0.003030962 | | | | | | | |
| Observations | 648 | | | | | | | |
| | | | | | | | | |
| ANOVA | | | | | | | | |
| | df | SS | MS | F | Significance F | | | |
| Regression | 1 | 0.202786303 | 0.202786303 | 22073.82531 | 0 | | | |
| Residual | 646 | 0.005934628 | 9.18673E-06 | | | | | |
| Total | 647 | 0.208720932 | | | | | | |
| | Coefficients | Standard Error | t Stat | P-value | Lower 95% | Upper 95% | Lower 95.0% | Upper 95.0% |
| Intercept | 0.002478915 | 0.00032486 | 7.630722314 | 8.40487E-14 | 0.001841006 | 0.003116823 | 0.001841006 | 0.003116823 |
| X Variable 1 | 0.948085602 | 0.006381294 | 148.5726264 | 0 | 0.93555502 | 0.960616185 | 0.93555502 | 0.960616185 |

FIG. 7A

| SUMMARY OUTPUT | | | | | | | | |
|---|---|---|---|---|---|---|---|---|
| *Regression Statistics* | | | | | | | | |
| Multiple R | 0.958496256 | | | | | | | |
| R Square | 0.918715073 | | | | | | | |
| Adjusted R Square | 0.918589245 | | | | | | | |
| Standard Error | 1.037520851 | | | | | | | |
| Observations | 648 | | | | | | | |
| | | | | | | | | |
| ANOVA | | | | | | | | |
| | df | SS | MS | F | Significance F | | | |
| Regression | 1 | 7859.537824 | 7859.537824 | 7301.352919 | 0 | | | |
| Residual | 646 | 695.3863881 | 1.076449517 | | | | | |
| Total | 647 | 8554.924212 | | | | | | |
| | Coefficients | Standard Error | t Stat | P-value | Lower 95% | Upper 95% | Lower 95.0% | Upper 95.0% |
| Intercept | 0.767597817 | 0.116018003 | 6.616194172 | 7.74127E-11 | 0.539779828 | 0.995415806 | 0.539779828 | 0.995415806 |
| X Variable 1 | 0.923616154 | 0.010809108 | 85.44795444 | 0 | 0.902390925 | 0.944841382 | 0.902390925 | 0.944841382 |

SYSTEM AND METHOD FOR ASSESSING REAL TIME PULMONARY MECHANICS

This application is a National Stage Application of International Application Number PCT/US2010/062232, filed Dec. 28, 2010; which claims the benefit of U.S. Provisional Application 61/290,392, filed Dec. 28, 2009 and U.S. Provisional Application No. 61/309,979, filed Mar. 3, 2010; all of which are incorporated herein by reference in their entirety.

FIELD OF THE INVENTION

The present invention relates generally to the field of respiratory therapy and physiology, including ventilator and respiratory monitor technology, and, more particularly, to a method and system for calculating respiratory system compliance ($C_{RS}$), resistance ($R_{RS}$) and inspiratory plateau pressure ($P_{plt}$) without the need to modify or interrupt the ventilator or patient air flow pattern.

BACKGROUND

Mechanical ventilatory support is widely accepted as an effective means for mechanically assisting or replacing spontaneous breathing. Mechanical ventilation can be non-invasive, involving various types of face masks or nasal devices, or invasive, involving endotracheal tube (ETT) or tracheal intubation. Selection and use of appropriate ventilatory techniques require an understanding of pulmonary mechanics.

Normal spontaneous inhalation generates negative intrapleural pressure, which creates a pressure gradient between the atmosphere and the alveoli, resulting in air inflow. During mechanical ventilation, the inspiratory pressure gradient is normally the result of or augmented by increased (positive) pressure of the air source. For patients requiring ventilatory support it is necessary to monitor both $C_{RS}$ and $_{RRS}$ to properly assess and treat the patient's pulmonary dysfunction or respiratory failure. Monitoring $P_{plt}$ is common practice to ensure the lung is not damaged via overdistention or over-pressurization during mechanical ventilation.

$R_{RS}$ is the amount of pressure required to force a given flow of gas though the combined series resistances of the breathing circuit, ETT resistance, and physiologic airways of a mechanically ventilated patient. $C_{RS}$ is a measurement of the distensibility of the lung, meaning the elastic recoil of the lungs and the chest wall for a given volume of gas delivered. Thus, for any given volume, elastic pressure is increased by lung stiffness (as in pulmonary fibrosis) or restricted excursion of the chest wall or diaphragm (i.e., tense ascites, massive obesity). Typically, $C_{RS}$ and $R_{RS}$ are calculated using an end inspiratory pause (EIP) during a constant inspiratory flow rate. $C_{RS}$ is estimated by dividing the delivered tidal volume by inspiratory $P_{plt}$, where $P_{plt}$ is the steady-state pressure measured during an EIP.

$R_{RS}$ is estimated by dividing the difference between peak inflation pressure (PIP) and $P_{plt}$ by the inspiratory flow rate. Some ventilators have an inspiratory flow rate setting such that the clinician can read the delivered flow rate while others dve an inspiratory time setting where the clinician needs to divide the tidal volume by the inspiratory time to determine the inspiratory flow rate.

Thus, $P_{plt}$ is essential for calculating $C_{RS}$ and $R_{RS}$. Moreover, monitoring $P_{plt}$ is also essential to avoid the over-distension of the alveoli, thus avoiding baro- and/or volutrauma, especially in patients with restrictive lung diseases (ARDS network protocol (July 2008); http://www.ardsnet.org/node/77791). In determining $P_{plt}$, current practice requires an EIP be performed. For patients with respiratory failure, this can be accomplished by applying an EIP immediately following a tidal volume during controlled mechanical ventilation (CMV) or intermittent mandatory ventilation (IMV).

Unfortunately, there are many drawbacks to having to perform an EIP. For one, the duration of EIP must be preset by a knowledgeable clinician and applied during mandatory breaths only while monitored. Temporary disruption of inhalation and prevention of exhalation by applying an EIP can be uncomfortable for some patients, causing the patient to involuntarily or voluntarily make active inspiratory or expiratory muscle contractions at the time of EIP, which can affect the accuracy of measured $P_{plt}$. If an imprecise measurement for $P_{plt}$ is obtained, resultant estimations for $C_{RS}$ and $R_{RS}$ would also be inaccurate. Because, as noted above, patient respiratory therapy and treatment are based on $C_{RS}$ and $R_{RS}$ values, erroneous calculations for $C_{RS}$ and $R_{RS}$ due to imprecise $P_{plt}$ measurements could subsequently affect the efficacy of treatment delivered to the patient and the patient's recovery, perhaps even to the detriment of the patient's health.

Further, because performing an EIP can be uncomfortable to the patient, it cannot be applied continuously. Without continuous, accurate $P_{plt}$ information, the clinician is unable to fully monitor patient safety and the efficacy of treatment.

Temporary disruption of inhalation by applying an EIP may also predispose to patient-ventilator dysynchrony. This may lead to increased work of breathing, and the possibility of compromising arterial blood-gas exchange.

Finally, an EIP may not be applied (or may be inaccurate) during pressure support ventilation (PSV), continuous airway procedure (CPAP), or other ventilatory modes which do not employ a constant inspiratory flow rate during the inhalational phase. Because of the inability to apply an EIP in these situations, clinicians are precluded from accurately assessing a patient's $P_{plt}$, $C_{RS}$ and $R_{RS}$ when ventilated with these modalities. Without correct assessment of patient $P_{plt}$, $C_{RS}$ and $R_{RS}$, efficacy of therapy and/or appropriate diagnosis of pulmonary disease or condition cannot be determined.

Thus, repeated accurate measurements of $P_{plt}$, and therefore $C_{RS}$ and $R_{RS}$, are difficult to obtain using EIP. If $P_{plt}$ could be determined without the need of applying an EIP, then more accurate estimations of $C_{RS}$ and $R_{RS}$ can be performed, even in real-time, precluding the need to interrupt the inhalation phase. Such an approach would be simpler and preferred, for both the clinician and the patient, and therefore needed in clinical practice.

In addition, knowledge of $P_{plt}$ during PSV would provide continuous monitoring of $C_{RS}$ and $R_{RS}$, and preclude the need to change ventilator modes.

Accordingly, there is a need in the art for a system and method to noninvasively, in real time accurately calculate $P_{plt}$, $C_{RS}$, and $R_{RS}$ without the need to modify ventilator inspiratory flow waveform pattern which may cause adverse effects such as patient-ventilator dysynchrony. A continuous, real time, and accurate understanding of the effects of mechanical ventilation and other therapeutic interventions (for example bronchodilators and airways suctioning) on pulmonary mechanics (i.e., $C_{RS}$ and $R_{RS}$) is needed to promote patient-ventilator synchrony and arterial blood-gas exchange. The present invention is designed to address this need.

SUMMARY OF THE INVENTION

The present invention provides a method and apparatus for non-invasively accurately calculating, in real time, $P_{plt}$, $C_{RS}$, and $R_{RS}$ without the need to interrupt or modify breathing in any manner. Accurate calculation of these respiratory parameters provides the ability to accurately determine other information that is valuable in treating a ventilated patient. In one embodiment, accurate and useful values for $P_{plt}$, $C_{RS}$, and $R_{RS}$ are estimated in real time via a processing system.

The subject invention is particularly advantageous in that it can utilize commonly measured respiratory parameters (i.e., airway pressure and flow rate over time during inspiratory phase of mechanical ventilation) to generate accurate, real time estimates of pulmonary mechanics, including but not limited to $P_{plt}$, $C_{RS}$ and $R_{RS}$. The resultant pulmonary mechanics estimates are particularly useful in real time monitoring of patient reaction to mechanical ventilation mode changes, the effects of various interventions (i.e., drugs) on pulmonary mechanics and physiology, the risks of lung overdistension, and the adequacy of lung protection strategies. Accurate and real time estimates of $P_{plt}$, $C_{RS}$, and $R_{RS}$ are also useful during pressure regulated ventilation commonly utilized for weaning to assist spontaneous breathing.

In one aspect of the invention, the method comprises creating a mathematical model of the patient's expiratory time constant ($\tau_E$) of the respiratory system by using predetermined parameters that are collected non-invasively, such as those collected with standard respiratory monitors. Such parameters include, but are not limited to, exhalation volume, airflow rate and pressure.

Respiratory monitors and ventilators typically contain airway pressure and airway flow sensors that measure the flow going into and out of the lungs, and often times they also contain a carbon dioxide sensor and pulse oximeter. From these time-waveforms, a variety of parameters are selectively derived that are used in characterizing different aspects of the patient's breathing and/or the patient's interaction with the ventilator. These parameters contain information that is extracted to accurately estimate the patient's inspiratory and expiratory flow and pressure waveform data. With the patient's inspiratory waveform data and $\tau_E$, accurate and continuous calculation in real time of estimates of patient inspiratory $P_{plt}$, and further patient $C_{RS}$, $R_{RS}$, and derivative pulmonary mechanics are accomplished. All of these estimates are useful for determining appropriate therapy, including ventilator settings.

In a one embodiment, real time $P_{plt}$, and patient $C_{RS}$ and $R_{RS}$ and derivative pulmonary mechanics, are accurately and continuously estimated using $\tau_E$ from passive deflation of the lungs during all modes of breathing. More preferably, real time $P_{plt}$, and patient $C_{RS}$ and $R_{RS}$ and derivative pulmonary mechanics, are accurately and continuously estimated using $\tau_E$ from passive deflation of the lungs during pressure regulated breathing.

The methods described herein may use a linear combination of parameters or a nonlinear combination of parameters, including but not limited to a neural network, fuzzy logic, mixture of experts, or polynomial model. Moreover, multiple different models can be used to estimate the pulmonary mechanics of different subsets of patients. These subsets can be determined by various means, including but not limited to patient condition (pathophysiology), patient physiologic parameters (i.e., inspiratory flow rate, airway resistance, tidal volume, etc.), or other parameters, such as ventilator parameters (i.e., positive end-expiratory pressure or PEEP, patient airway inflation pressure, etc.).

In a preferred aspect of the invention, the method for calculating the pulmonary mechanics involves the application of a uniquely derived set of equations based on the standard patient airway equation during inhalation and exhalation, combined with equations for the computation of the expiratory time constant. A fundamental aspect of this methodology is the calculation of a time constant from the exhalation portion of the waveform (e.g., pressure, flow, volume, etc.) followed by the use of this expiratory time constant and data from a one or more instances of time in the inspiratory time waveforms (e.g. airway pressure, flow, and volume at a defined time t) to calculate $P_{plt}$, $R_{RS}$ and $C_{RS}$. In a preferred embodiment, a single instance of time from the inspiratory time waveform is a time of low patient effort, typically found in the early or late portion of the inspiratory waveform. Since patient effort is unknown and typically unmodeled, finding the point of lowest patient effort will increase the accuracy of the parameter estimation.

In a another aspect of the invention, the method for calculating the pulmonary mechanics in a patient comprises use of a neural network, wherein the neural network provides the pulmonary mechanics information for the patient based upon input data, wherein the input data includes at least one of the following parameters: the airway pressure, flow, airway volume, expiratory carbon dioxide flow waveform, and pulse oximeter plethysmogram waveforms normally collected by a respiratory monitor, including but not limited to tidal volume, breathing frequency (f), PIP, inspiratory time, $P_{0.1}$, inspiratory trigger time, trigger depth, wherein accurate and useful estimates for $\tau_E$, $P_{plt}$, $C_{RS}$, and $R_{RS}$ are provided as an output variable.

In the aforementioned method, the neural network is trained by clinical testing of a test population of patients to obtain teaching data, the teaching data which includes the above-noted input information. The teaching data are provided to the neural network, whereby the neural network is trained to provide an output variable corresponding to $C_{RS}$, and $R_{RS}$.

The invention can be implemented in numerous ways, including as a system (including a computer processing or database system), a method (including a computerized method of collecting and processing input data and a method for evaluating such data to provide an output(s)), an apparatus, a computer readable medium, a computer program product, or a data structure tangibly fixed in a computer readable memory. Several embodiments of the invention are discussed below.

As a system, an embodiment of the invention includes a processor unit having input and output devices. The processor unit operates to receive input parameters, process the input and provide an output corresponding to pulmonary mechanics information. This output can be then used to control external devices, such as a ventilator. The processing of the data can be accomplished by various means such as microcontrollers, neural networks, parallel distributed processing systems, neuromorphic systems, or the like.

As a method of accurately calculating in real time patient's $P_{plt}$, $C_{RS}$, $R_{RS\,and}\tau_E$, the subject invention includes processing predetermined input variables (parameters) using the formulas described herein, preferably through the use of a computer readable media program containing program instructions, a processing system, or a neural network.

As a computer readable media containing program instructions, an embodiment of the invention includes: computer readable code devices for receiving input variables, processing the input, and providing an output indicative of $C_{RS}$ and $R_{RS}$. In a preferred embodiment, processing comprises utilizing a neural network. The method may further include controlling a ventilator in response to the output obtained.

The methods of the present invention may he implemented as a computer program product with a computer-readable medium having code thereon. The program product includes a program and a signal bearing media bearing the program.

As an apparatus, the present invention may include at least one processor, a memory coupled to the processor, and a program residing in the memory which implements the methods of the present invention.

Other aspects and advantages of the invention will become apparent from the following detailed description taken in conjunction with the accompanying drawings, illustrating, by way of example, the principles of the invention.

All patents, patent applications, provisional applications, and publications referred to or cited herein, or from which a claim for benefit of priority has been made, are incorporated herein by reference in their entirety to the extent they are not inconsistent with the explicit teachings of this specification.

BRIEF DESCRIPTION OF THE DRAWINGS

FIG. 6A is the regression analysis of calculated $P_{plt}(\tau_F)$ versus measured Pplt, note that $r^2$=0.99 (p<0.001).

FIG. 7A is the regression analyses of $C_{RS}$ from $\tau_E$ compared to $C_{RS}$ from $P_{plt}$, note that $r^2$=0.97 (p<0.001).

FIG. 8A is the regression analyses of $R_{RS}$ from $\tau_E$ compared to $R_{RS}$ from $P_{plt}$, note that $r^2$=0.92 (p<0.001).

DETAILED DESCRIPTION

Figure 1:
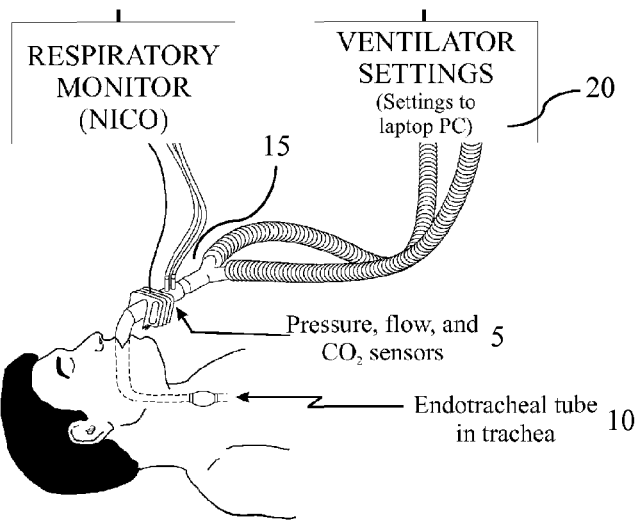
FIG. 1 is an illustration of a patient whose pulmonary mechanics are estimated in accordance with the subject invention.

Current standard estimates of $P_{plt}$, $C_{RS}$, and $R_{RS}$ are obtained in patients during positive pressure inflation and by measuring lung inflation pressure during an EIP, i.e., a pause for at least 0.5 seconds). Unfortunately, there are several disadvantages to performing an EIP, including patient discomfort, requirement for clinician input and careful monitoring, imprecise measurements due to patient interference, patient-ventilator dysynchrony, inability to be applied continuously, and inability to perform EIP with certain forms of ventilation. To address these deficiencies, the subject invention provides systems and methods for accurately calculating estimated $P_{plt}$, $C_{RS}$, and $R_{RS}$ values using a modified estimate of $\tau_E$ from passive lung deflation, obviating the need for an EIP. The result is a continuous, real time estimate of pulmonary mechanics that can monitor breath to breath lung function and the effect of therapeutic interventions.

Inspiratory $P_{plt}$ is an important parameter to calculate a patient's $C_{RS}$ and $R_{RS}$ during mechanical ventilation. Monitoring $P_{plt}$ is also essential to avoid the over-distension of the alveoli, thus avoiding baro- and/or volutrauma, especially in patients with restrictive lung diseases (ARDS network protocol (July 2008); http://www.ardsnet.org/node/77791).

According to the subject invention, the method for estimating, accurately and in real time, pulmonary mechanics for patients receiving mechanical ventilation, or any device that interfaces with patient pulmonary system, involves the following steps: (a) receiving respiratory parameters of a patient; (b) calculating, with a processor, a modified $\tau_E$ from the respiratory parameters; (c) inputting the modified $\tau_E$ into a mathematical model; and (d) providing at least one output variable from the mathematical model corresponding to $P_{plt}$, $C_{RS}$ and/or $R_{RS}$, or other pulmonary mechanics.

In one embodiment, the mathematical model is a neural network trained to provide the estimated pulmonary mechanics. The neural network can be trained to include clinical testing of a population of subjects using monitored ventilator pressure and flow as clinical data input to the neural network.

The $\tau_E$ of passive lung exhalation is a parameterization of the time needed to complete exhalation based on an expontial decay and contains information about the mechanical properties of the respiratory system (Guttmann, J. et al., "Time constant/volume relationship of passive expiration in mechanically ventilated ARDS patients," *Eur Respir J.*, 8:114-120 (1995); and Lourens, M S et al., "Expiratory time constants in mechanically ventilated patients with and without COPD," *Intensive Care Med*, 26(11):1612-1618 (2000)). $\tau_E$ is defined as the product of the $C_{RS}$ and $R_{RS}$ (Brunner, J X et al., "Simple method to measure total expiratory time constant based on the passive expiratory flow volume curve," *Crit Care Med*, 23:1117-1122 (1995)). $\tau_E$ can be estimated in real-time by simply dividing the exhalation volume (V(t)) by exhalation flow ($\dot{V}_{exh}(t)$) i.e., ($\tau_E(t)=V(t)/\dot{V}_{exh}(t)$ (Brunner, J X et al., "Simple method to measure total expiratory time constant based on the passive expiratory flow volume curve," *Crit Care Med,* 23:1117-1122 (1995); and Guttmann, J. et al., "Time constant/volume relationship of passive expiration in mechanically ventilated ARDS patients," *Eur Respir J.,* 8:114-120 (1995)). This method gives an estimate of $\tau_E$ for each point during exhalation.

Unfortunately, current methods for estimating $\tau_E$ are somewhat inaccurate, particularly with patients connected to mechanical ventilators, because of possible interference from the ventilator's exhalation valve during initial opening. Further, current estimates of $\tau_E$ include a portion of the end of exhalation, which (1) can cause observable late (slow) compartment kinetic behavior of $\tau_E$ that may be attributed to the viscoelastic properties of the respiratory system that can be inaccurate because of alveolar emptying inequalities within the lung (pendelluft effect) (Guerin, C. et al., "Effect of PEEP on work of breathing in mechanically ventilated COPD patients," *Intensive Care Med,* 26(9):1207-1214 (2000)); and (2) creates less stable values of $V(t)/\dot{V}_{exh}(t)$ due to reduced flow at the end of exhalation and the division by numbers near zero. In addition, because the resistance of the ventilator's exhalation valve becomes more significant at the end of exhalation, that too can affect whether an accurate estimate of $\tau_E$ is determined using current methods.

Accordingly, in one embodiment of the invention, a more accurate, modified estimate of $\tau_E$ is achieved by utilizing the expiratory waveform only during the middle and more reliable portion of exhalation. For example, averaging the exhalation waveform slope from 0.1 to 0.5 seconds after the beginning of exhalation (e.g., mean function) is one method for obtaining a more reliable estimate of $\tau_E$. The first part of exhalation (between 0 and 0.1 sec) is excluded to reduce possible interference from the ventilator's exhalation valve during initial opening as well as residual patient effort. The end of exhalation (beyond 0.5 sec) is excluded to address issues attributable to end exhalation as described above.

Figure 13:
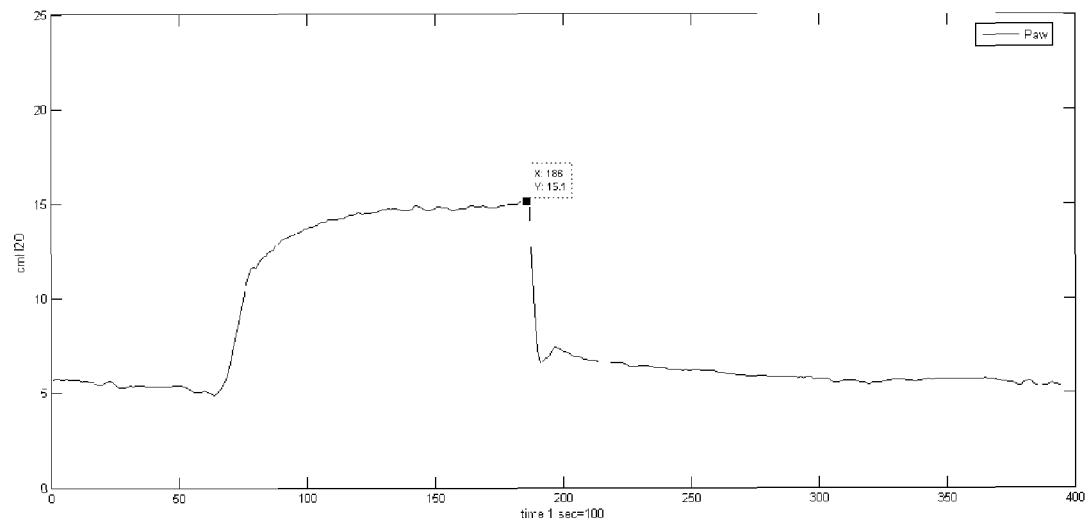
FIG. 13 is a graphical illustration of variable patient effort while on pressure support ventilation.
Figure 14:
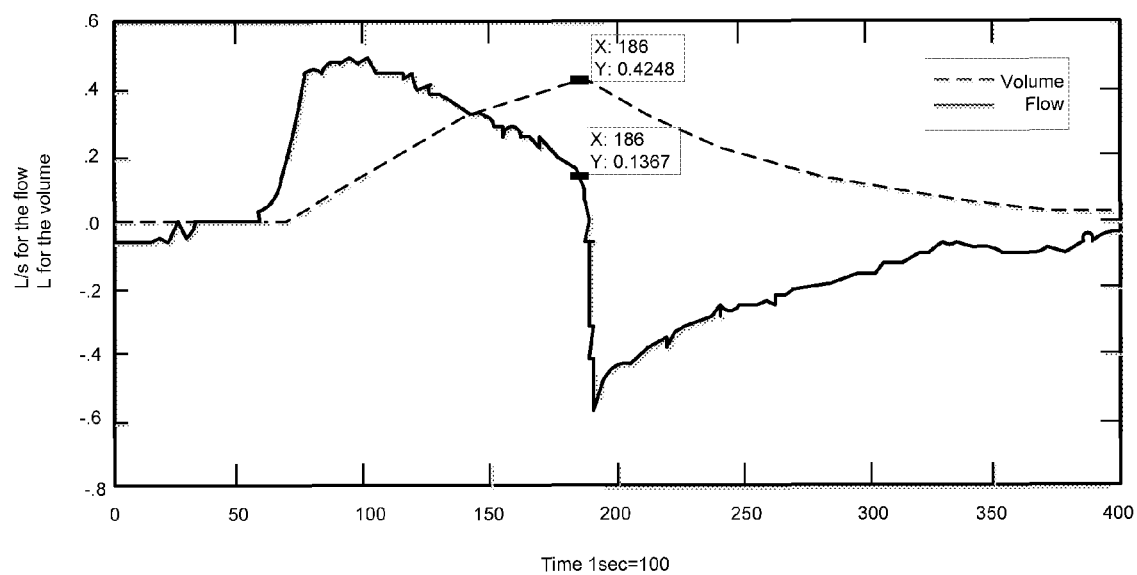
FIG. 14 provides graphical illustrations of flow and volume curves for the same breath illustrated in FIG. 13.

FIGS. 13 and 14 are graphical illustrations of various respiratory parameters useful in calculating $P_{plt}$, $R_{RS}$ and $C_{RS}$. FIG. 13 shows a breath from variable patient effort while on pressure support ventilation (PSV) mode. The label shows the last point of inhalation on the airway pressure curve (Paw), which represents the least patient effort and is utilized to estimate $P_{plt}$, $R_{RS}$ and $C_{RS}$.

FIG. 14 shows the flow and volume curves for the same breath in FIG. 13. The labeled points are the points where values associated with pulmonary mechanics ($P_{plt}$, $R_{RS}$ and $C_{RS}$) are calculated. These points correspond to the last point of inhalation on the Paw curve. As illustrated in FIG. 14, calculations for $P_{plt}$, $R_{RS}$ and $C_{RS}$ based upon estimated $\tau_E$ are usually confined to flow higher than 0.1 L/sec. Another approach for a more accurate estimate of $\tau_E$ involves a median function. For example, a more accurate estimate of $\tau_E$ can be derived by taking the average or median of multiple $\tau_E$ estimates during exhalation. Advantageously, limiting the locations where these time constant estimations are made provides better time constant values. High flow and low flow regions of exhalation are more likely to produce erroneous estimations and are therefore excluded.

Figure 15:
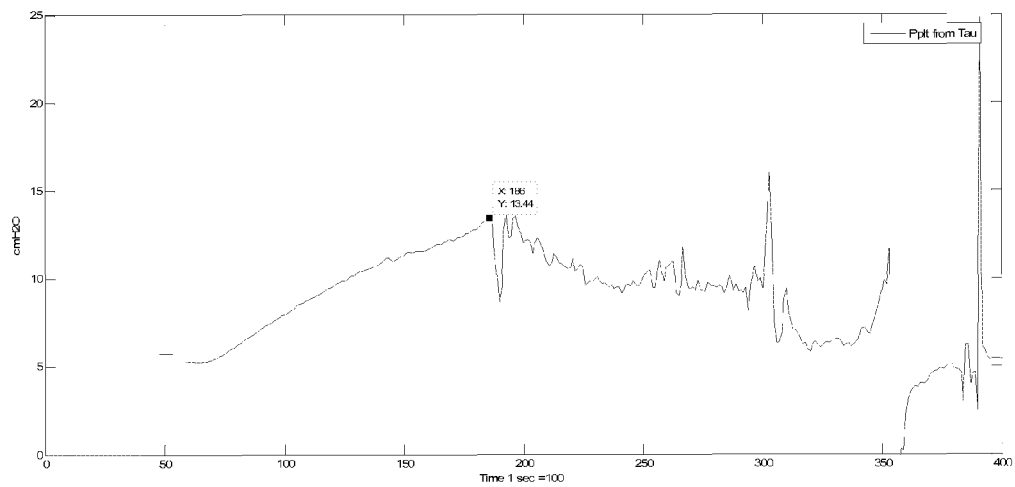
FIG. 15 is a $P_{plt}$ curve calculated at every point of inhalation.

FIG. 15 shows a $P_{plt}$ curve, where $P_{plt}$ was calculated from $\tau_E$ estimates at every point of inhalation (and exhalation, which should be excluded). The label on the $P_{plt}$ curve is on the last valid portion of inhalation, which corresponds to the end of inhalation illustrated in FIG. 14.

In certain embodiments, the median of $\tau_E$ estimates utilizing the portion of exhalation where flow is less than 80% of peak inspiratory flow but greater than 0.1 LPS provide a more accurate estimate of $\tau_E$. In another embodiment, several estimates of the time constant for multiple breaths can be averaged or median filtered to provide a better estimate of $\tau_E$ for a region of breaths.

In alternate embodiments, the exhalation portion can be defined by percentage of volume exhaled. In certain embodiments, the median of $\tau_E$ estimates from different combinations of percentages of volume and/or peak expiratory flow provide more accurate estimates of $\tau_E$. In one embodiment, the percentage from the peak expiratory flow lies between 95% and 20% of the peak expiratory flow. In another embodiment, the percentage from the peak expiratory flow lies between 95% and 70% of the peak expiratory flow. In yet another embodiment, the portion of exhalation between 80% of exhaled volume and 20% of exhaled volume is utilized.

Because resistance is a function of flow and $\tau_E$ is a function of resistance, $\tau_E$ values may vary with flow rate. In another embodiment, better $\tau_E$ estimates can be achieved by selecting areas of exhalation to estimate $\tau_E$ based on the inspiratory flow rates. For example, better $\tau_E$ estimates can be achieved in those ventilation modes where the inspiratory flow rates are constant such as IMV, VC+(Volume Control Plus), or Assist Control.

During exhalation, the resistance portion of $\tau_E$ calculated in a mechanically ventilated patient is the sum of three series resistances i.e., total resistance ($R_{TOT}$), which is the sum of physiologic airways resistance ($R_{aw}$), imposed resistance of the endotracheal tube ($R_{ETT}$), and ventilator exhalation valve resistance ($R_{vent}$).

$$R_{TOT}=R_{aw}+R_{ETT}+R_{vent}$$

According to the subject invention, the resistance applied by the ventilator exhalation valve can be excluded from the estimate of $\tau_E$ as derived above for improved, accurate modified estimates of $\tau_E$.

Thus, the $R_{vent}$ can be calculated by:

$$R\text{vent}(t)=(Paw(t)-PEEP)/\dot{V}_{exh}(t)$$

where Paw is airway pressure, PEEP is positive end expiratory pressure (if applied, zero otherwise), and $\dot{V}_{exh}(t)$ is exhaled airway flow rate.

To calculate the more accurate, modified $\tau_E$ estimate of the invention, $\tau_E$ total (t) is first calculated as described above. Then, the following equations derive an equation for the patient's $\tau_E$ that excludes ventilator resistance:

$$C_{est}=(VT+\tau_E\text{total}*\dot{V}_{exh}(t))/(Paw-PEEP),$$

where $C_{est}$ is the estimated compliance from $\tau_E$ total, then $$\tau_E\text{total}(t)=(R_{RS}(t)+R\text{vent}(t))*C_{est}$$

$$\tau_E\text{total}(t)=(R_{RS}(t)*C_{est})+(R\text{vent}(t)C_{est})$$

Utilizing $C_{est}$ as an estimate for $C_{rs}$ produces the following more accurate estimate of the time constant:

$$\tau_E(t)=\tau_E\text{total}(t)-(R\text{vent}(t)*C_{est})$$

Once the $\tau_E$ is estimated and corrected as taught above, inspiratory waveform data are utilized to estimate $P_{plt}$, $R_{RS}$, $C_{RS}$ and other pulmonary mechanics.

$C_{RS}$ and $R_{RS}$, and thus $P_{plt}$, can be accurately estimated in accordance with the invention as follows:

Calculating $C_{RS}$ is derived as follows:

$$Paw-PEEP=V_T/C_{RS}+R_{RS}*\dot{V}_{inj}: \text{airway equation}$$

$$C_{RS}(Paw-PEEP)=V_T+R_{RS}*C_{RS}*\dot{V}_{inh}: \text{multiply both sides by } C_{RS} \text{ to derive the following equation for } C_{RS}:$$

$$C_{RS} = \frac{V_T + \tau_E \times \dot{V}_{inh}}{P_{aw} - PEEP}$$

Where $P_{aw}$ is airway inflation pressure, PEEP is positive end expiratory pressure, $V_T$ is tidal volume, and $\dot{V}_{inh}$ inspiratory flow rate.

Calculating $R_{RS}$ involves the following equations:

$$Paw - PEEP = V_T/C_{RS} R_{RS} * \dot{V}_{inh}: \text{airway equation}$$

$$Paw - PEEP = V_T * R_{RS}/C_{RS} + R_{RS} * \dot{V}_{inh}: \text{multiply } V_T/C_{RS} \text{ by } R_{RS}/R_{RS}$$

$$Paw - PEEP = R_{RS}(V_T/\tau_E + \dot{V}_{inh}): \text{simplify right side to derive the following equation for } R_{RS}:$$

$$R_{RS} = \frac{P_{aw} - PEEP}{\dfrac{V_T}{\tau_E} + \dot{V}_{inh}}$$

Calculating Pplt involves the following equations:

$$P_{plt} = (V_T/C_{Rs}) + PEEP$$

Or alternatively, $$P_{plt} = \frac{V_T \times P_{aw} - V_T \times PEEP}{(V_T + \tau_E * \dot{V}_{inh}) + PEEP}$$

As a further refinement of the methodology above, it should be noticed that $\tau_E$ varies with flow since resistance varies widely with flow. As such, an error in $\tau_E$ estimate can be predicted as (Peak inspiratory flow (PIF)–Peak expiratory flow (PEF)) varies. To correct for this error, a correction factor to $R_{RS}$ component of $\tau_E$ can be applied. This correction factor will likely depend on the mode of ventilation, amount of patient effort, PIF and PEF. However, a reasonable correction factor for the patients described in FIG. 5 was found to be y=5.2487*(PIF−PEF)−0.8393. According to the subject invention, peak inspiratory flow (PIF)−peak expiratory flow (PEF) then becomes the correction factor for $\tau_E$.

In the equations above, it is important to realize that the flow, pressure, and volume values utilized are not waveforms, but are single measurements. In the preferred embodiment, these measurements occur simultaneously so that the volume, flow, and pressure values are associated with a single point in time during inhalation. Since the airway equation does not include a term for inspiratory effort generated by the patient's inspiratory muscles, the ideal location to measure these values is when the inspiratory effort is minimal (to avoid the errors caused by inspiratory effort in the airway equation). As such, the preferred point where these measurements are made are the point during inhalation with minimal effort. Locating the point of minimal patient effort, however, can be difficult because instantaneous patient effort can only be accurately calculated by invasive methods such as esophageal pressure catheters. In a typical breath, however, low patient effort often occurs near the end (or sometimes at the beginning) of inspiration.

With the expiratory time constant, individual estimates of plateau pressure, resistance, compliance and related respiratory parameters can be estimated at each point of the inspiratory waveforms. Estimating these parameters throughout inhalation provides useful information including flow-dependent resistance estimates and varying estimates of compliance, plateau pressure, and other parameters throughout the breath. The data from these estimates throughout estimation can be valuable to better estimate other derived parameters including but not limited to patient effort, more accurate average resistance and compliance, and accurate triggering information.

In one embodiment a point of minimum effort for accurate parameter estimation is determined by calculating $P_{plt}$ curves throughout inhalation and utilizing the point where $P_{plt}$ was at its maximum. In another embodiment, a point of low patient effort is located by finding the position during inspiration where compliance is at its minimum value. Both of these embodiments rely on the fact that patient effort will tend to increase the estimate of compliance and decrease the plateau pressure.

Figure 16:
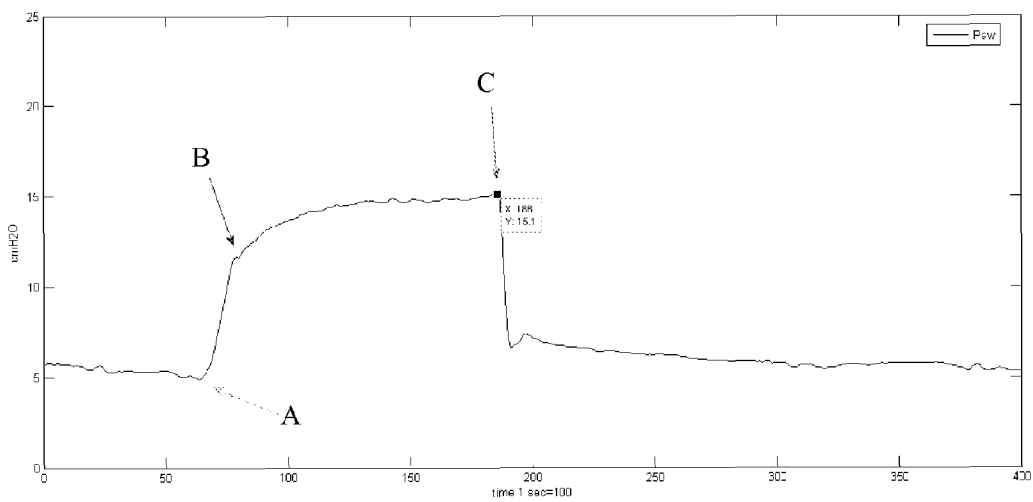
FIG. 16 is an airway pressure curve in which valid points for compliance estimation are indicated.
Figure 17:
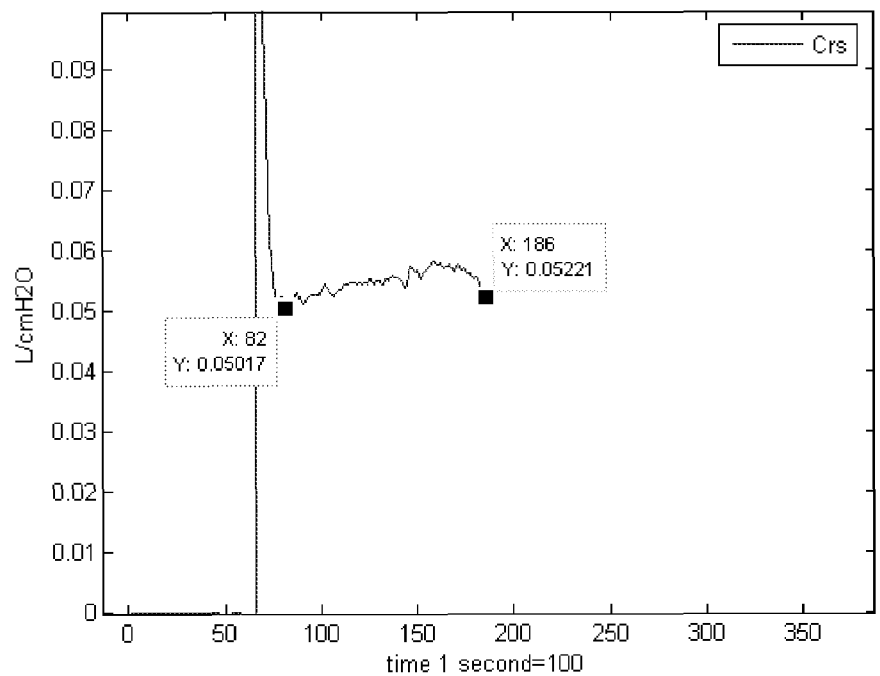
FIG. 17 is a $C_{RS}$ curve, where points that can be used for accurate estimation of the pulmonary parameters are indicated.
Figure 18:
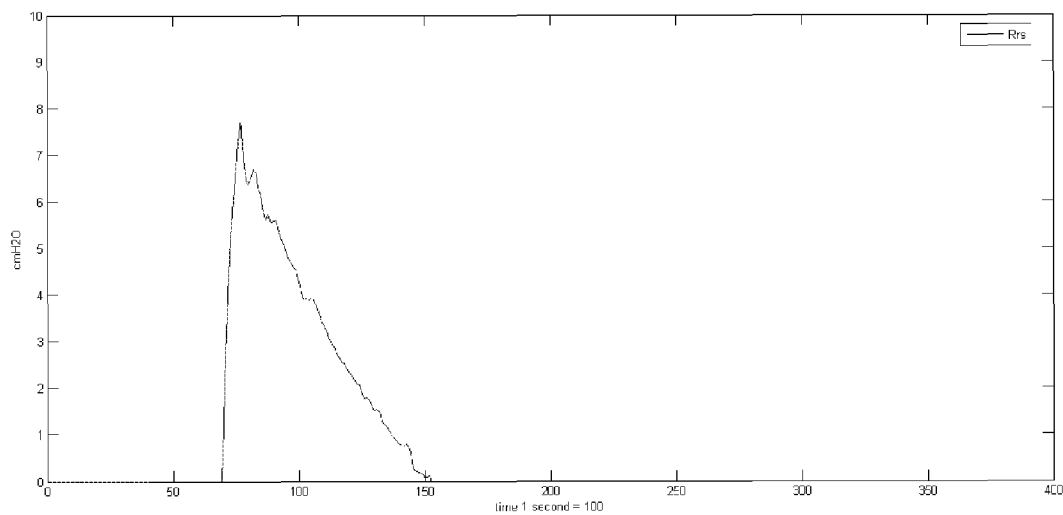
FIG. 18 is a $R_{RS}$ (resistance) curve from the inhalation portion of the breath illustrated in FIG. 16.

For example, points A, B, and C in FIG. 16 provide examples of points of compliance that can be used to identify volume, flow and pressure values in calculating $\tau_E$, $P_{plt}$, $R_{RS}$ and $C_{RS}$. FIG. 17 shows compliance calculated during the breath and two minimum points (as labeled x=82 and x=186) that can be used for accurate estimation of pulmonary parameters. FIG. 18 shows the resistance curve from the inhalation portion of this breath. Resistance is flow dependent, so as flow decreases, resistance will as well.

Figure 19A:
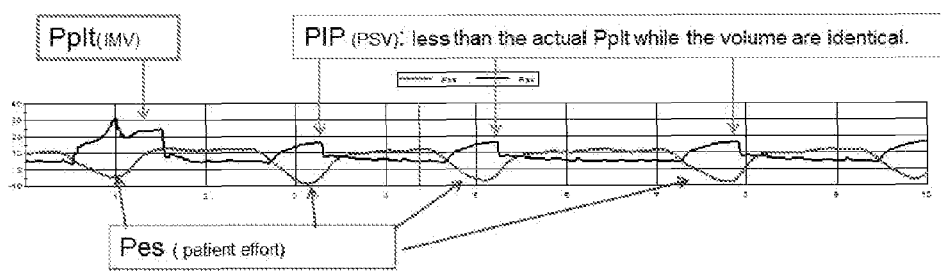
FIG. 19A is a graphical illustration of airway pressure (Paw; dark line curve) and Pes (esophageal pressure; light line curve).
Figure 19B:
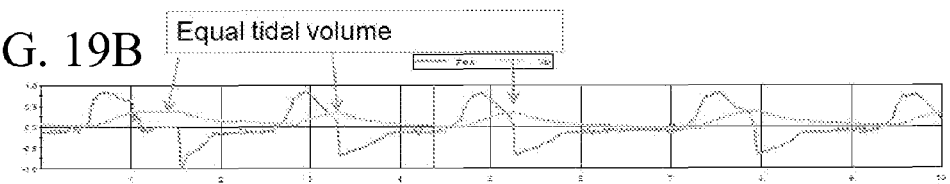
FIG. 19B is a diagram illustrating flow (dark line curve) and volume (light line curve

FIGS. 19A and B illustrate patient data with high inspiratory effort during PSV augmented by low IMV rate. The first breath (on the left) is a control breath (IMV) that has the same tidal volume of the PSV breath. FIG. 19A is a diagram illustrating airway pressure (Paw; dark line curve) and Pes (esophageal pressure; light line curve). FIG. 19B is a diagram illustrating flow (dark line curve) and volume (light line curve).

In a real-time environment, some breaths are contaminated by coughing, the patient fighting the ventilator, poor triggering by the ventilator, sensor noise or errors, and other problems. As such, it is advantageous to reject breaths that are contaminated and lead to estimates that are outside a normal range. Averaging or utilizing median values of a group of non-contaminated breaths results provide a better overall estimate of the respiratory parameters. In one embodiment, breaths that had a compliance value outside the normal range were eliminated. In addition, common breath parameters are computed and compared against normal values. The breath parameters include peak inspiratory pressure, tidal volume, inspiratory time, expiratory time, mean airway pressure, and the like.

The estimated $P_{plt}$, $C_{RS}$, and $R_{RS}$ values determined in accordance with the methodologies described herein are particularly useful for any device that interfaces with patient pulmonary system. Contemplated devices include, but are not limited to, ventilators, respiratory monitors, pulmonary function machines, sleep apnea systems, hyperbaric devices, and the like. As understood by the skilled clinician, such devices include various sensors and/or processing system for providing data regarding patient respiratory parameters, such as airway pressure, flow, airway volume, tidal volume, f, PIP, inspiratory time, $P_{0.1}$, inspiratory trigger time, trigger depth, exhalation period, as well as airway, endotracheal tube, and ventilator exhalation valve resistances. Contemplated ventilators include those that accomplish any one or more of the following modes of ventilation: volume-cycled ventilation; assist-control ventilation (A/C); synchronized intermittent mandatory ventilation (SIMV); pressure-cycled ventilation; pressure support ventilation (PSV); pressure control ventilation (PCV); noninvasive positive pressure ventilation (NIPPY); and continuous positive airway pressure (CPAP) or bilevel positive airway pressure (BIPAP).

In one embodiment of the invention, continuous, real time estimates of $P_{plt}$, $C_{RS}$, and $R_{RS}$ are determined in order to diagnose pulmonary condition or disease (including apnea detection and treatment in obstructive sleep apnea as well as COPD and ARDS detection) and/or to assess intervention efficacy. For example, continuous accurate knowledge of patient $C_{RS}$ and $R_{RS}$ is particularly useful in establishing more accurate ventilator settings for the patient and in pharmaceutical applications (such as bronchodilators). Continuous and accurate knowledge of patient pulmonary mechanics during application of pharmaceuticals is particularly useful in assessing therapeutic efficacy and in determining proper dosage. In addition, the real-time data from this invention could be used to determine obstructions or obstacles from affecting the patient's ventilation. For instance, the invention can be utilized to determine when the breathing tube requires suctioning to remove mucus or other obstructions, or may determine when the tube may be kinked.

In another embodiment, real time estimates of $P_{plt}$, $C_{RS}$, and $R_{RS}$ are utilized to estimate or improve estimates of patient effort via the application of the airway equation (for example, calculating Pmus as the difference between the expected airway pressure and the actual airway pressure). This is also useful for determining and optimizing patient synchrony by allowing accurate measurement of the onset and offset of patient effort. Optimization of the ventilator on-triggering and off-triggering can be implemented either manually or automatically.

In another embodiment, the real time estimates are utilized to track the patient health and response to treatment. Compliance tracking during changes in PEEP indicate when the lung is being ventilated optimally. Changes in resistance indicate that drugs to relax the patient airway are working as expected. Utilizing the physiologic parameters allows for the titration and optimization of treatments, both via the ventilator and pharmaceutically.

In an embodiment, the model, such as a neural network, is pretrained with clinical data and the input parameters can be collected non-invasively with a standard respiratory monitor. The neural network is trained to predict the physiologic and imposed pulmonary mechanics using the non-invasively acquired parameters described above (although invasive parameters may be added to the system, if desired.) Once a model having a desired degree of predictability has been achieved and verified, the network output, such as an actual pulmonary mechanics variable may be used as an accurate predictor of patient pulmonary mechanics.

Description of Neural Networks

Artificial neural networks loosely model the functioning of a biological neural network, such as the human brain. Accordingly, neural networks are typically implemented as computer simulations of a system of interconnected neurons. In particular, neural networks are hierarchical collections of interconnected processing elements (PEs). These elements are typically arranged in layers, where the input layer receives the input data, the hidden layers transform the data, and the output layer produces the desired output. Other embodiments of a neural network can also be used.

Each processing element in the neural network receives multiple input signals, or data values, that are processed to compute a single output. The inputs are received from the outputs of PEs in the previous layer or from the input data. The output value of a PE is calculated using a mathematical equation, known in the art as an activation function or a transfer function that specifies the relationship between input data values. As known in the art, the activation function may include a threshold, or a bias element. The outputs of elements at lower network levels are provided as inputs to elements at higher levels. The highest level element, or elements, produces a final system output, or outputs.

Figure 9:
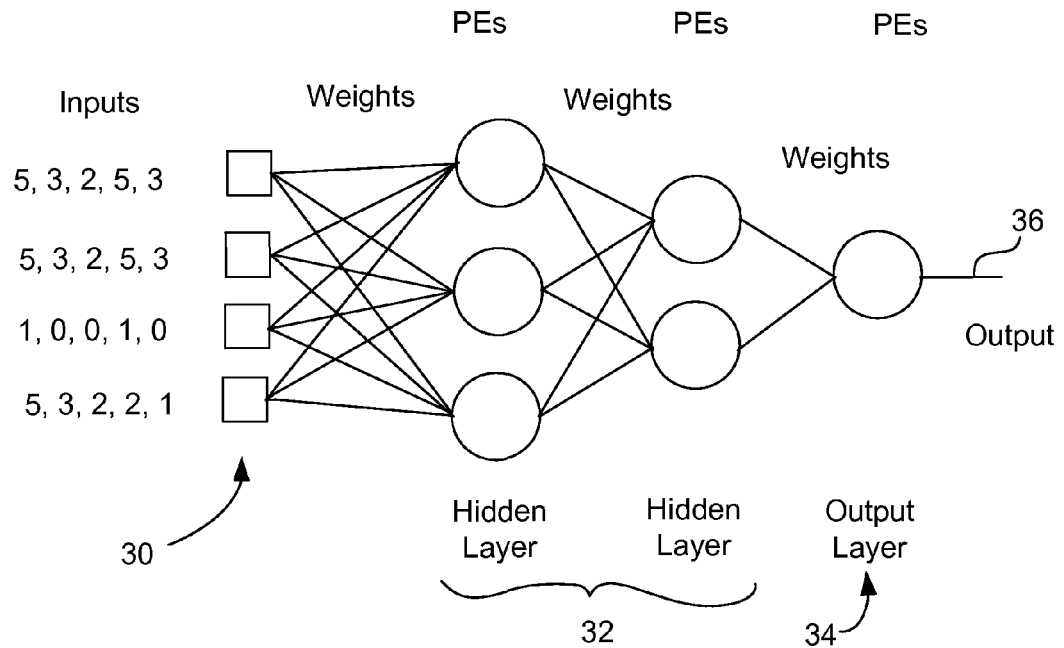
FIG. 9 depicts a neural network showing hidden layers.

In the context of the present invention, the neural network is a computer simulation that is used to produce a noninvasive estimate of the quantified patient effort described previously. The neural network of the present invention may be constructed by specifying the number, arrangement, and connection of the processing elements which make up the network. A simple embodiment of a neural network consists of a fully connected network of processing elements. As shown in FIG. 9, the processing elements of the neural network are grouped into the following layers: an input layer 30 where the parameters collected and/or derived from the airway pressure and flow sensors are inputted to the network; a hidden layer or layers 32 of processing elements; and an output layer 34 where the resulting prediction of patient effort 36 is produced. The number of connections, and consequently the number of connection weights, is fixed by the number of elements in each layer 30, 32, 34.

Figure 10:
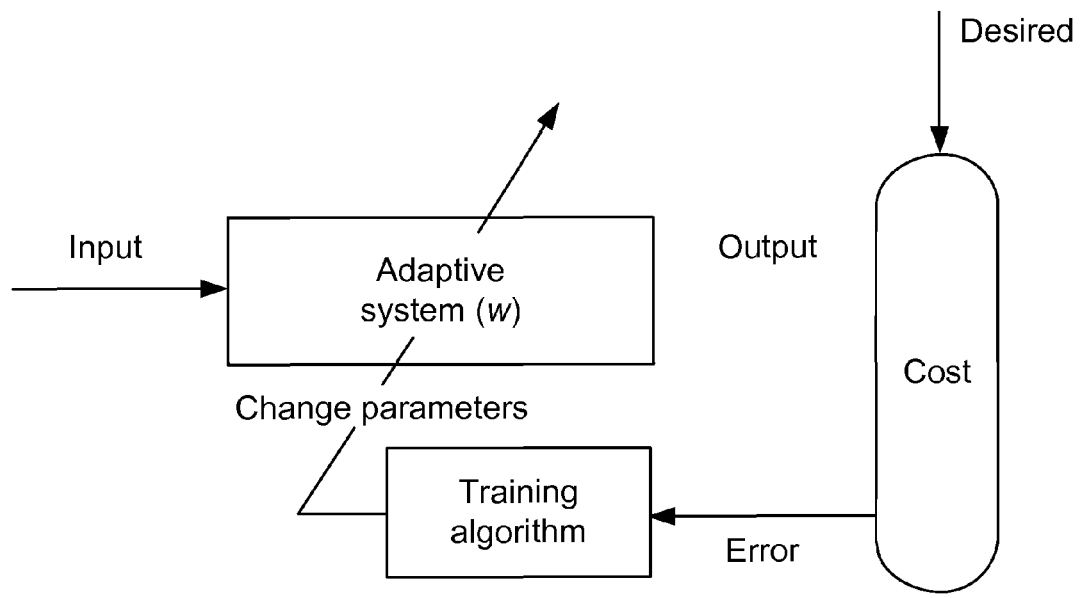
FIG. 10 depicts inputs and outputs of an adaptive system having back-propagation.

The most common training methodology for neural networks is based upon iterative improvement of the system parameters (normally called weights) by minimizing the mean squared difference between the desired output and the network output (mean squared error, MSE). The input is applied to the neural network, the neural network passes the data through its hierarchical structure, and an output is created. This network output is compared with the desired output corresponding to that input and an error is calculated. This error is then used to adjust the weights of the system so that the next time that particular input is applied to the system the network output will be closer to the desired output. There are many possible methodologies to adjust the weights, called the training algorithm. As shown in FIG. 10, the most common is called backpropagation that involves calculating each weight's responsibility for the error, and calculating a local gradient from this error in order to use a gradient descent learning rule for each weight.

Based on the foregoing specification, the invention may be implemented using computer programming or engineering techniques including computer software, firmware, hardware or any combination or subset thereof. Any such resulting program, having computer-readable code means, may be embodied or provided within one or more computer-readable media, thereby making a computer program product, i.e., an article of manufacture, according to the invention. The computer readable media may be, for instance, a fixed (hard) drive, diskette, optical disk, magnetic tape, semiconductor memory such as read-only memory (ROM), etc., or any transmitting/receiving medium such as the Internet or other communication network or link. The article of manufacture containing the computer code may be made and/or used by executing the code directly from one medium, by copying the code from one medium to another medium, or by transmitting the code over a network.

One skilled in the art of computer science will easily be able to combine the software created as described with appropriate general purpose or special purpose computer hardware to create a computer system or computer sub-system embodying the method of the invention. An apparatus for making, using or selling the invention may be one or more processing systems including, but not limited to, a central processing unit (CPU), memory, storage devices, communication links and devices, servers, I/O devices, or any subcomponents of one or more processing systems, including software, firmware, hardware or any combination or subset thereof, which embody the invention. User input may be received from the keyboard, mouse, pen, voice, touch screen, or any other means by which a human can input data into a computer, including through other programs such as application programs.

EXAMPLE 1

The subject systems and methods for accurately estimating in real time pulmonary mechanics based on monitored ventilation parameters was validated using a heterogenous population of thirty (30) adult patients in respiratory failure requiring mechanical ventilation, namely patients receiving positive pressure ventilation.

For each patient, $P_{plt}$ was recorded in the intermittent mandatory ventilation (IMV) mode with inspiratory flow waveform and an end inspiratory pause of 0.5 second. Inspiratory flow rate recorded ranged between 0.5 to 1.0 L/s).

Figure 2:
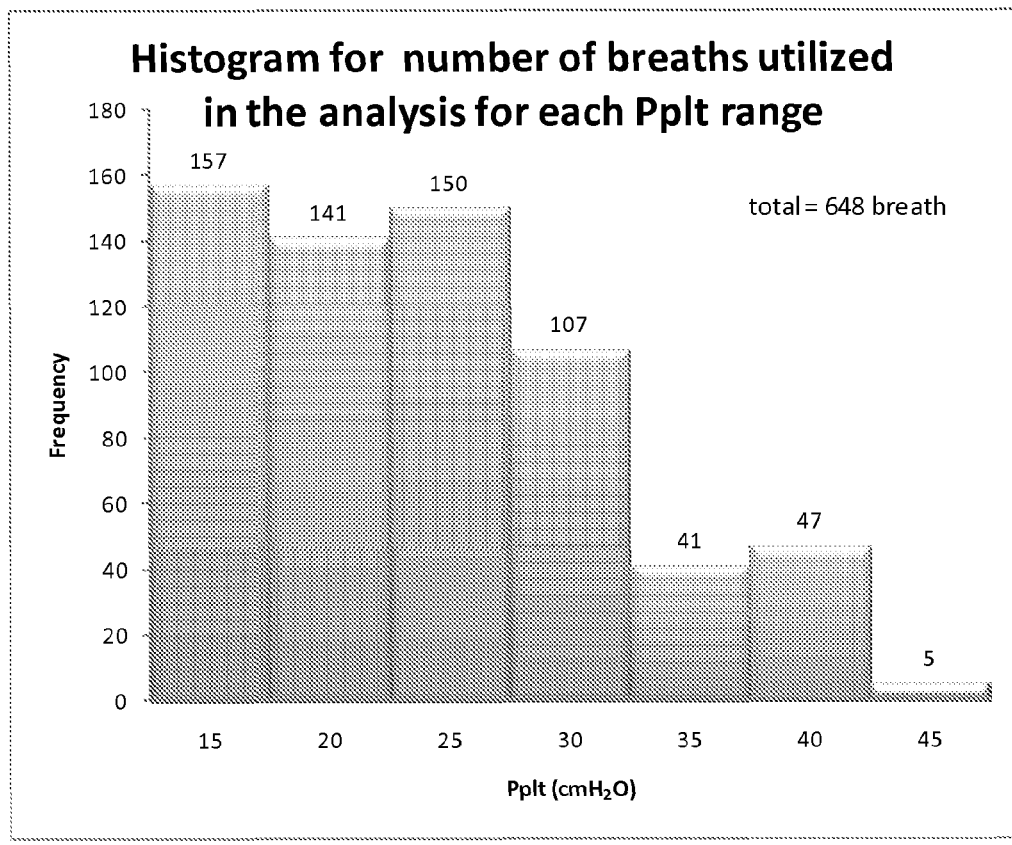
FIG. 2 is a histogram showing the relative frequency of $P_{plt}$ measurement in the group described in Example 1.
Figure 3:
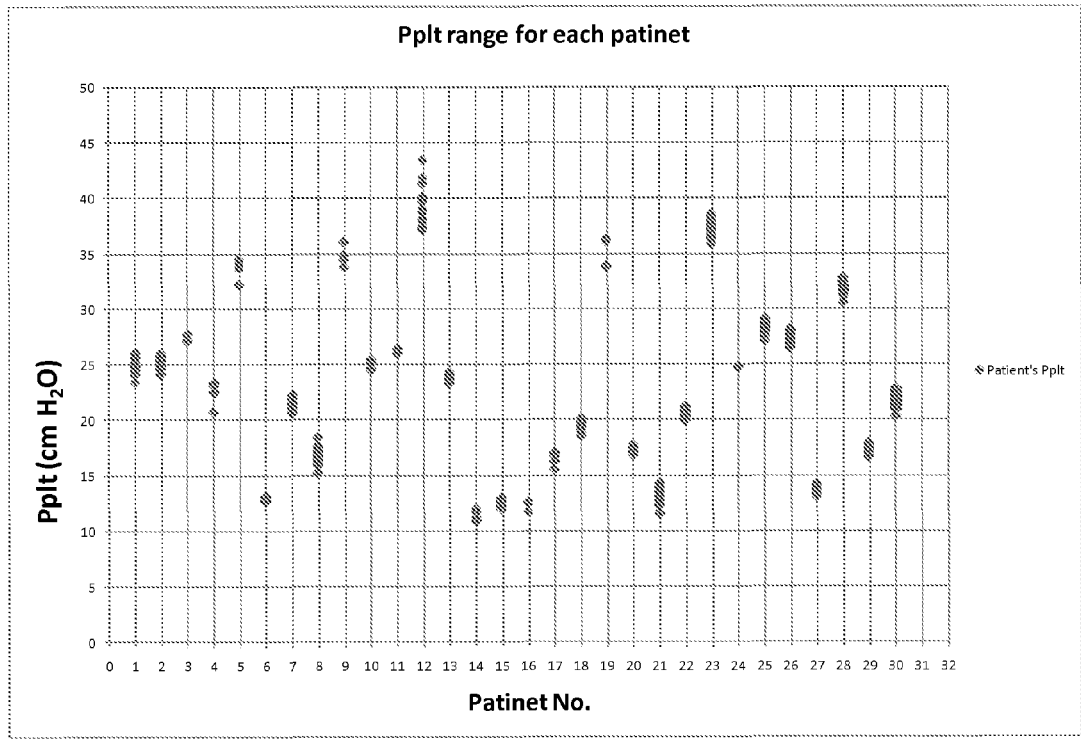
FIG. 3 is a graphical illustration of measured $P_{plt}$ ranges for each subject of Example 1.

As illustrated in FIG. 1, data from a combined pressure/flow sensor 5 (NICO, Respironics) positioned between the patient endotracheal tube 10 and Y-piece 15 of the ventilator breathing circuit, were directed to a laptop computer 20 with software performing the methods described herein (Convergent Engineering) for measurement and recording of pressure, flow, and volume data. As illustrated in Table 1 below and FIGS. 2 and 3, $P_{plt}$ data ranged from 10 to 44 cm $H_2O$ in the studied patient population.

TABLE 1

Patient Demographic

| Patient | Age (Years) | Height (Inches) | Weight (Kilograms) | Gender | ETT size (mm) |
|---|---|---|---|---|---|
| 1 | 74 | 62 | 68 | male | 7 |
| 2 | 37 | 68 | 62 | male | 8 |
| 3 | 37 | 74 | 204 | male | 7.5 |
| 4 | 53 | 71 | 108 | male | 8 |
| 5 | 67 | 64 | 60 | male | 7 |
| 6 | 69 | 70 | 71 | male | 8 |
| 7 | 68 | 65 | 68 | female | 8 |
| 8 | 51 | 72 | 80 | male | 8 |
| 9 | 37 | 66 | 69 | male | 8 |
| 10 | 67 | 72 | 83 | male | 8 |
| 11 | 20 | 73 | 223 | male | 8 |
| 12 | 62 | 59 | 60 | female | 7 |
| 13 | 73 | 68 | 89 | male | 8 |
| 14 | 18 | 67 | 60 | female | 7 |
| 15 | 60 | 70 | 60 | male | x |
| 16 | 20 | 64 | 62 | male | 7.5 |
| 17 | 50 | 70 | 63 | male | 8 |
| 18 | 54 | 70 | 80 | male | 7.5 |
| 19 | 68 | 65 | 50 | female | 7.5 |
| 20 | 48 | 72 | 76 | male | 8 |
| 21 | 47 | 69 | 66 | male | 7.5 |
| 22 | 26 | 71 | 74 | male | 8 |
| 23 | 48 | 72 | 76 | male | 8 |
| 24 | 72 | 74 | 90 | male | 8 |
| 25 | 75 | 65 | 76 | male | 7.5 |
| 26 | 18 | 73 | 100 | male | 8 |
| 27 | 63 | 69 | 70 | male | 7.5 |
| 28 | 50 | 67 | 75 | female | 7.5 |
| 29 | 25 | 71 | 86 | male | 8 |
| 30 | 70 | 72 | 83 | male | 8 |

Figure 4A:
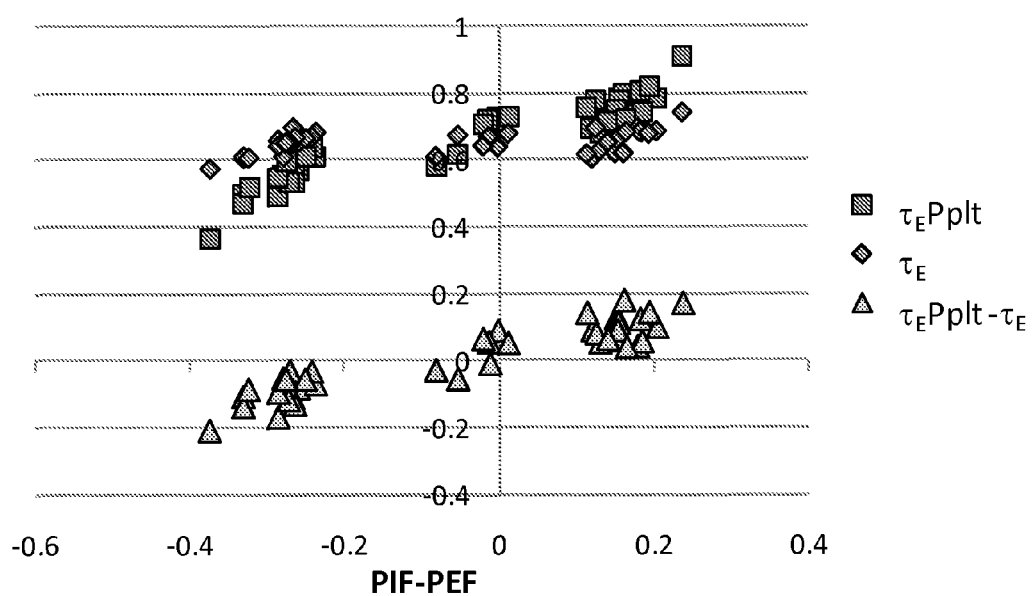
FIGS. 4A-4C are graphical illustrations of $\tau_E$ (blue diamonds) from three random subjects (A, B and C) with three different inhalational flows (0.5, 0.75 and 1 L/S) and compared with $\tau_E P_{plt}$ obtained by end inhalation pause (red squares) and the difference between $\tau_E P_{plt}$ and $\tau_E$ (green triangles) depending on the gap between PIF and PEF (X-axis). According to the subject invention, peak inspiratory flow (PIF)–peak expiratory flow (PEF) then becomes the correction factor for $\tau_E$, where $\tau_E P_{plt} = R_{RS} * C_{RS}$.
Figure 4B:
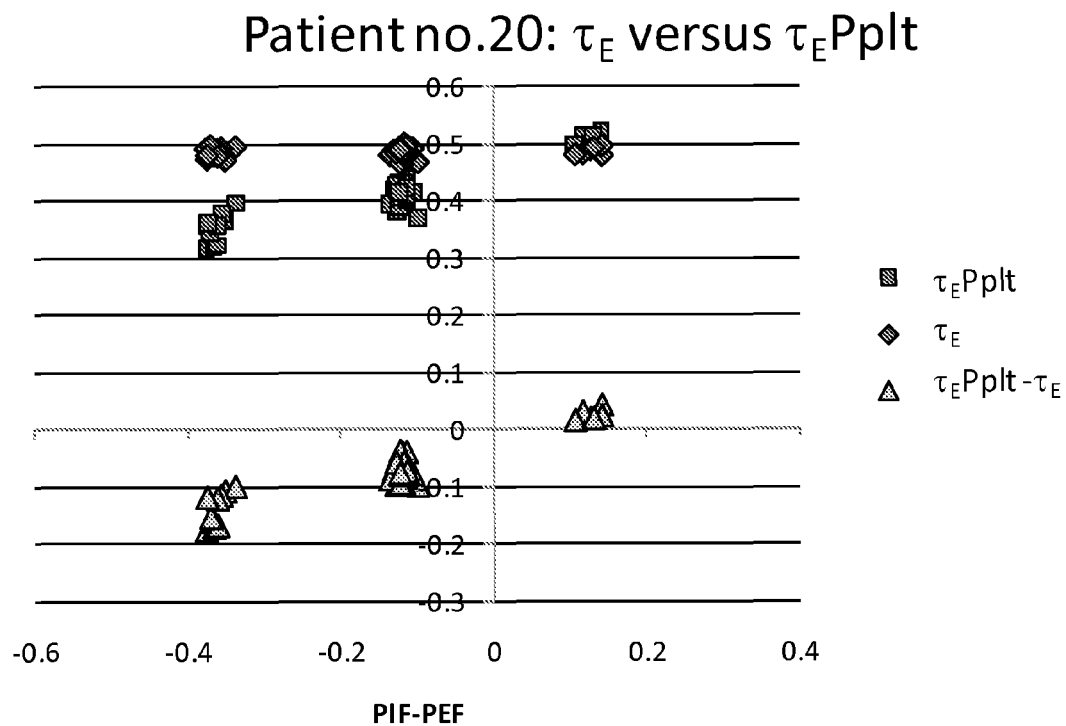
Figure 4C:
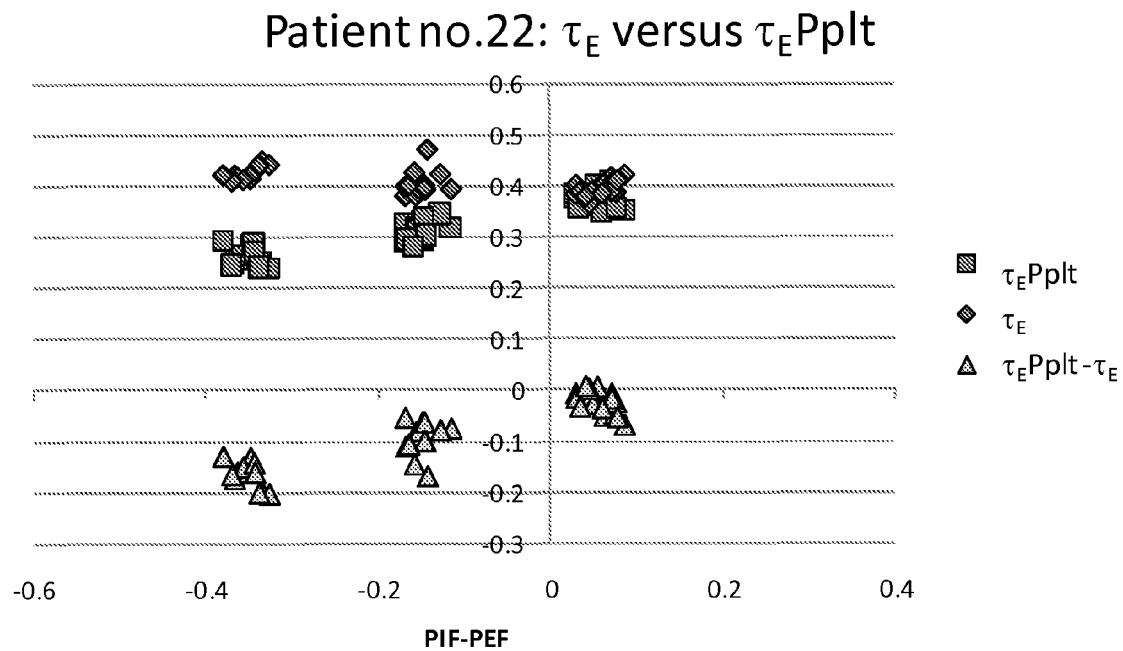

$\tau_E$ was obtained from three random patients (A, B and C) with three different inhalational flows (0.5, 0.75 and 1 L/S) and compared with $\tau_E P_{plt}$ obtained by an end inhalation pause (EIP). As illustrated in FIGS. 4A-4C, $\tau_E P_{plt}$ differs from $\tau_E$ depending on the gap between PIF and PEF (X-axis). $\tau_E$ is represented in FIGS. 4A-4C as blue diamonds and $\tau_E P_{plt}$ as red squares, where the difference in $\tau_E P_{plt}$ from $\tau_E$ is represented as green triangles. PIF-PEF then becomes the correction factor for $\tau_E$ (Guerin, C. et al., "Effect of PEEP on work of breathing in mechanically ventilated COPD patients," *Intensive Care Med*, 26(9):1207-1214 (2000).

Figure 5:
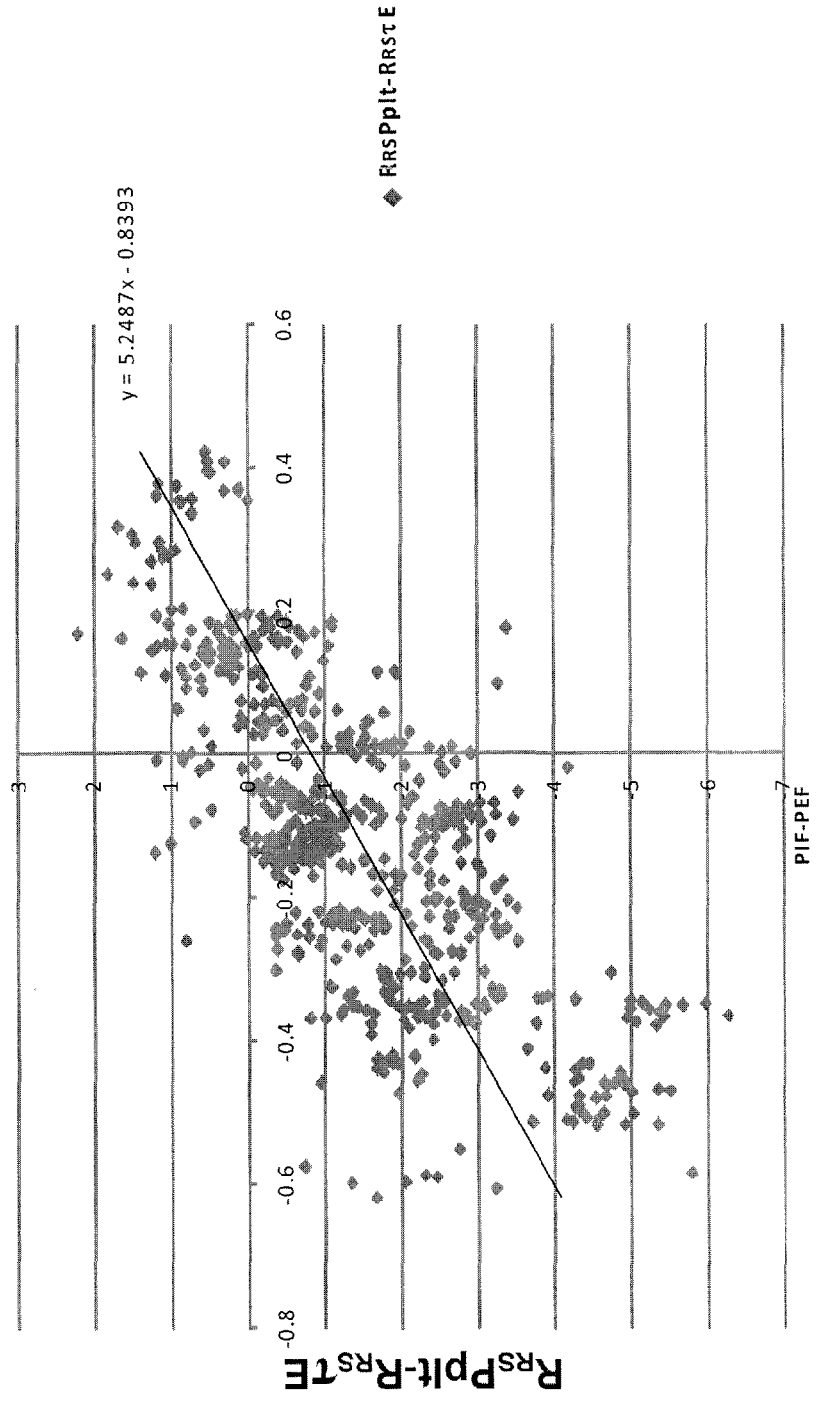
FIG. 5 is a graphical illustration of the effect of flow difference (PIF–PEF) on inhalation and exhalation $R_{RS}$ ($R_{RS}P_{plt} - R_{RS}\tau_F$), where the equation y=5.2487x−0.8393 was used as a correction factor for the flow difference $R_{RS}$, where y is the corrected factor for $R_{RS}\tau_E$, and x is PIF–PEF.

To derive the effect of flow difference of peak inspiratory flow rate and peak expiratory flow rate (PIF-PEF) on inhalation and exhalation, $R_{RS}$ ($R_{RS}$ $P_{plt}$-$R_{RS}\tau_E$), the equation y=5.2487*(PIF-PEF)-0.8393 was used as a correction factor for the flow difference $R_{RS}$. FIG. 5 the effect of flow difference on inhalation, where PIF=peak inspiratory flow rate, PEF=peak expiratory flow rate, $R_{RS}P_{plt}$=patient $R_{RS}$ from Pplt, $R_{RS}\tau_E$=patient $R_{RS}$ from $\tau_E$.

Figure 6B:
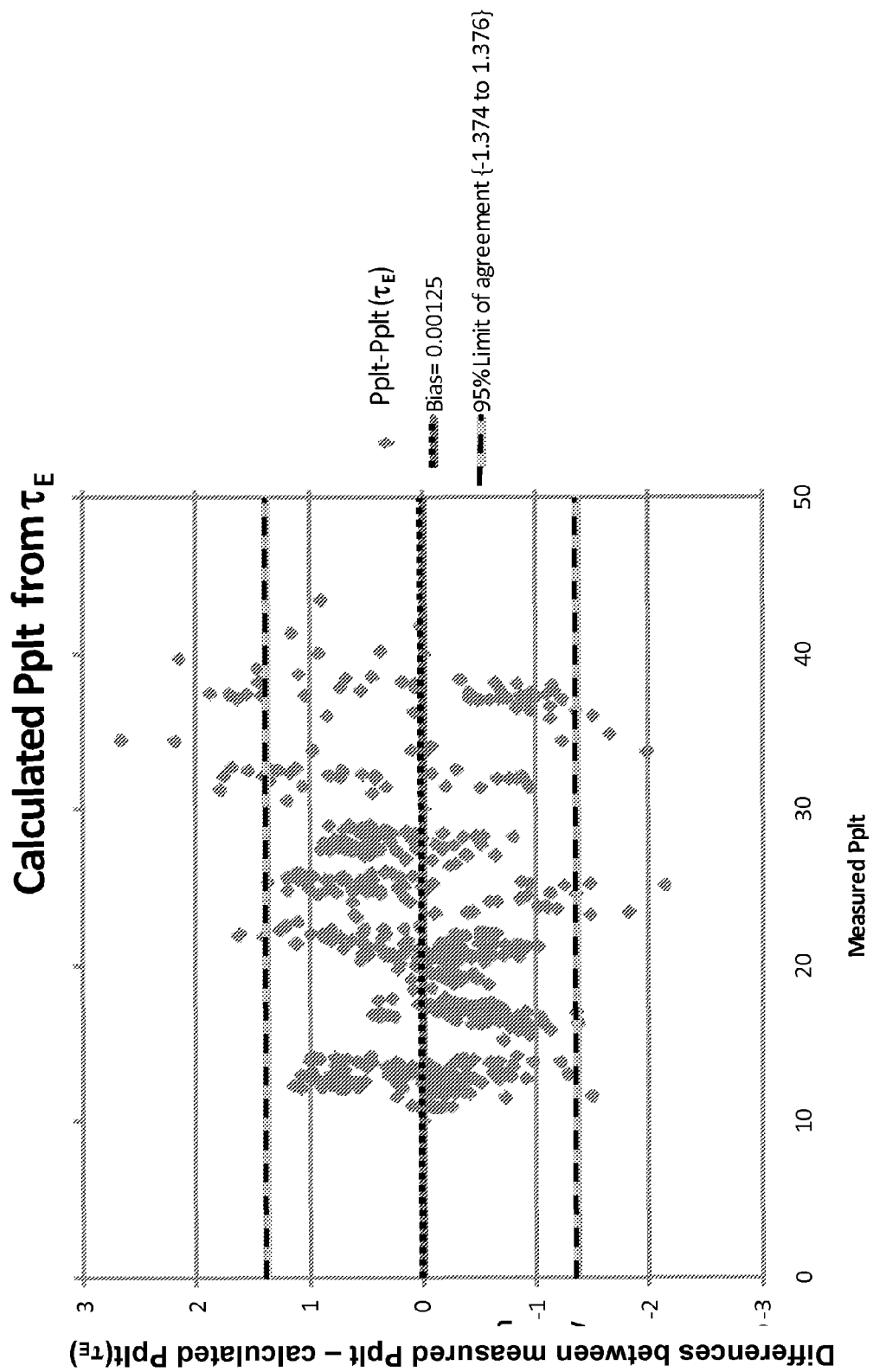
FIG. 6B is a Bland-Altman graph showing the difference between calculated $P_{plt}(\tau_E)$ and measured $P_{ply}$, bias is essentially zero and precision of measurement is excellent.
Figure 6C:
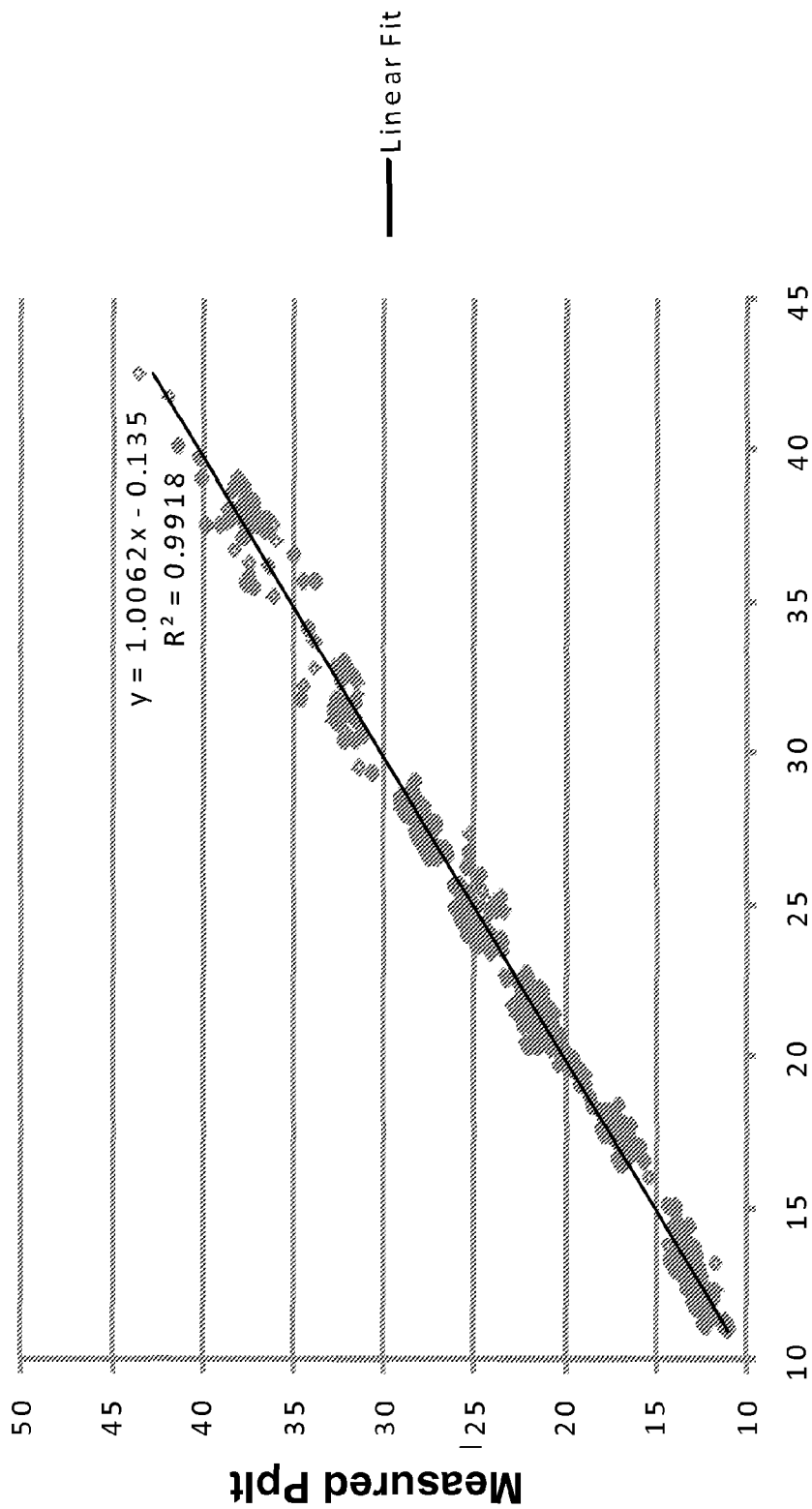
FIG. 6C is a linear fit graph between calculated $P_{plt}(\tau_E)$ and measured $P_{plt}$, note that $r^2$=0.99.

Analysis of Validation Data:

A regression analysis between the calculated and actual (end inspiratory pause) Pplt, which includes the correction calculated above, is illustrated in the table in FIG. 6A. Illustrated in FIG. 6B is a Bland-Altman graph showing the difference between $r^2$ correlation is 0.99, Bias=0.00125, 95% limit of agreement=-1.347 to 1.376. FIG. 6C illustrates the linear fit diagram displaying proportional value=1.006.

Figure 7B:
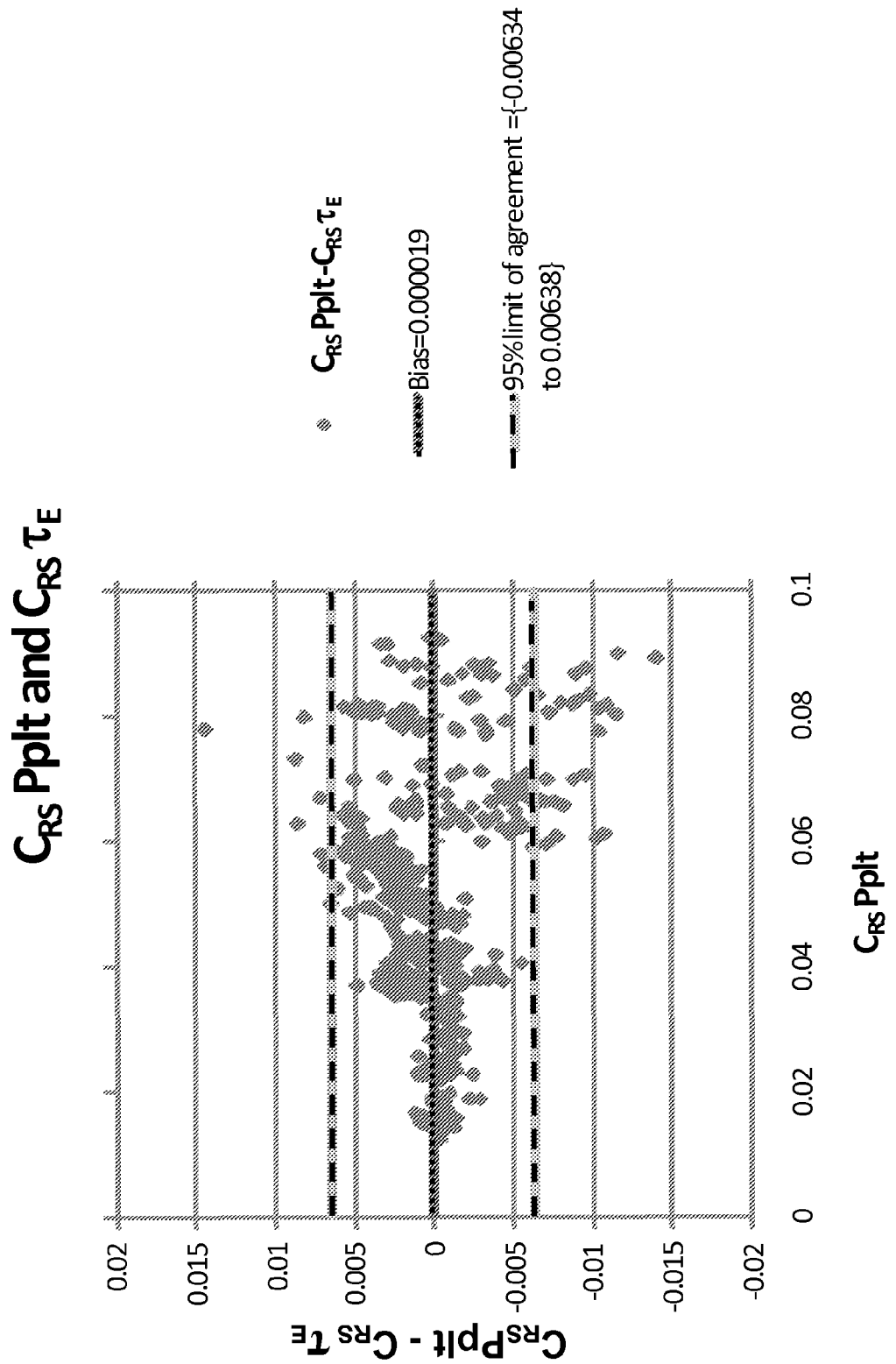
FIG. 7B is a Bland-Altman graph showing the difference between $C_{RS} P_{plt}$ and $C_{RS}\tau_E$, bias is essentially zero and precision of measurement is excellent.
Figure 7C:
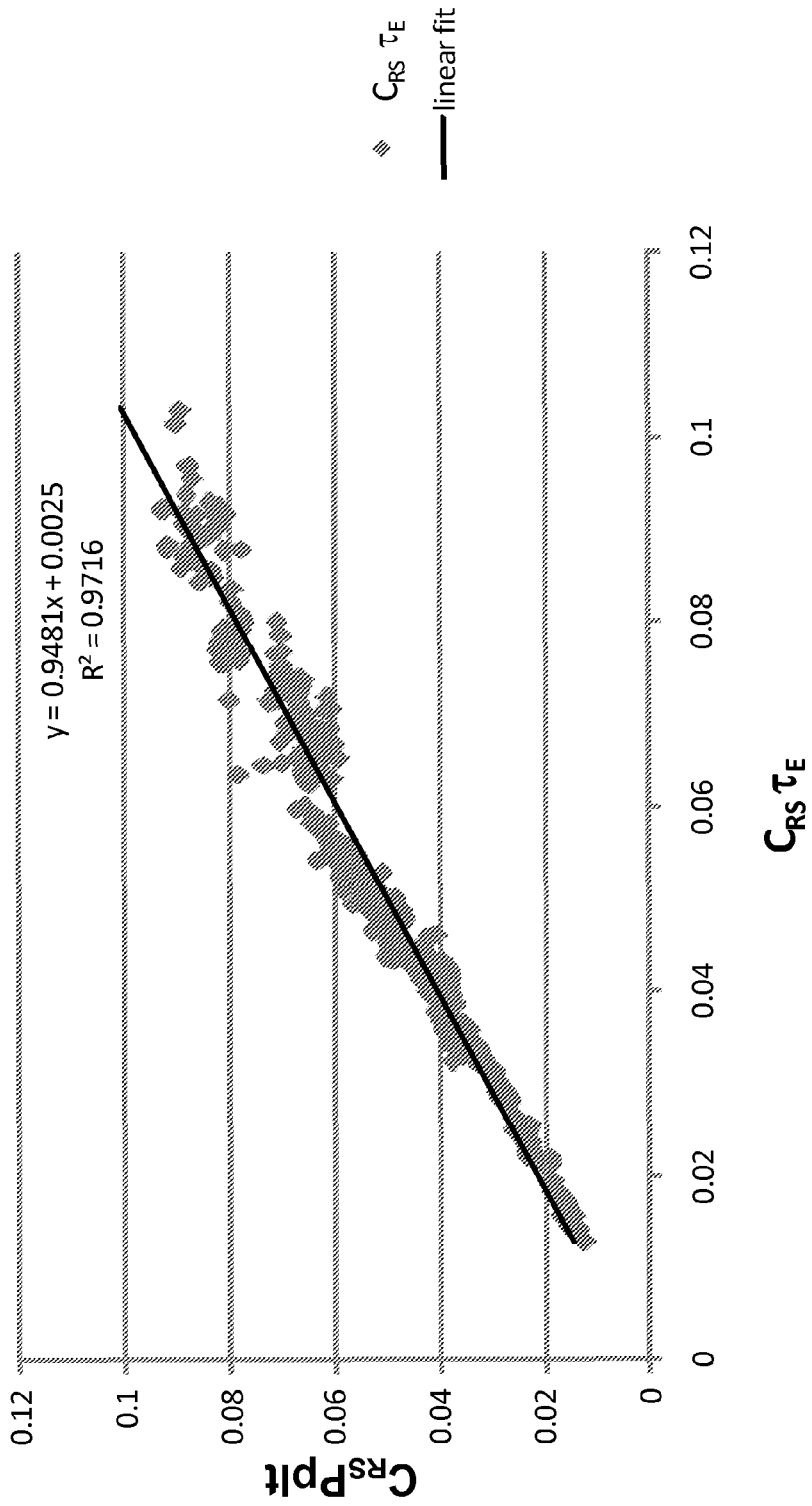
FIG. 7C is a linear fit graph between $C_{RS} \tau_E$ and $C_{RS} P_{plt}$.

Analysis of $C_{RS}$ calculation:

FIG. 7A is a graphical illustration of a regression analysis between calculated $C_{RS}$ from $\tau_E$ compared with the standard calculated $C_{RS}$ from $P_{plt}$, where r2=0.97. FIG. 7B illustrates a Bland-Altman graph of the difference between $C_{RS}P_{plt}$ and $C_{RS}\tau_E$, where Bias=0.0000199, 95% limit of agreement={-0.00634 to 0.00638}. FIG. 7C is a linear fit graph between $C_{RS}\tau_E$ and $C_{RS}P_{plt}$, where Proportional=0.948.

Figure 8B:
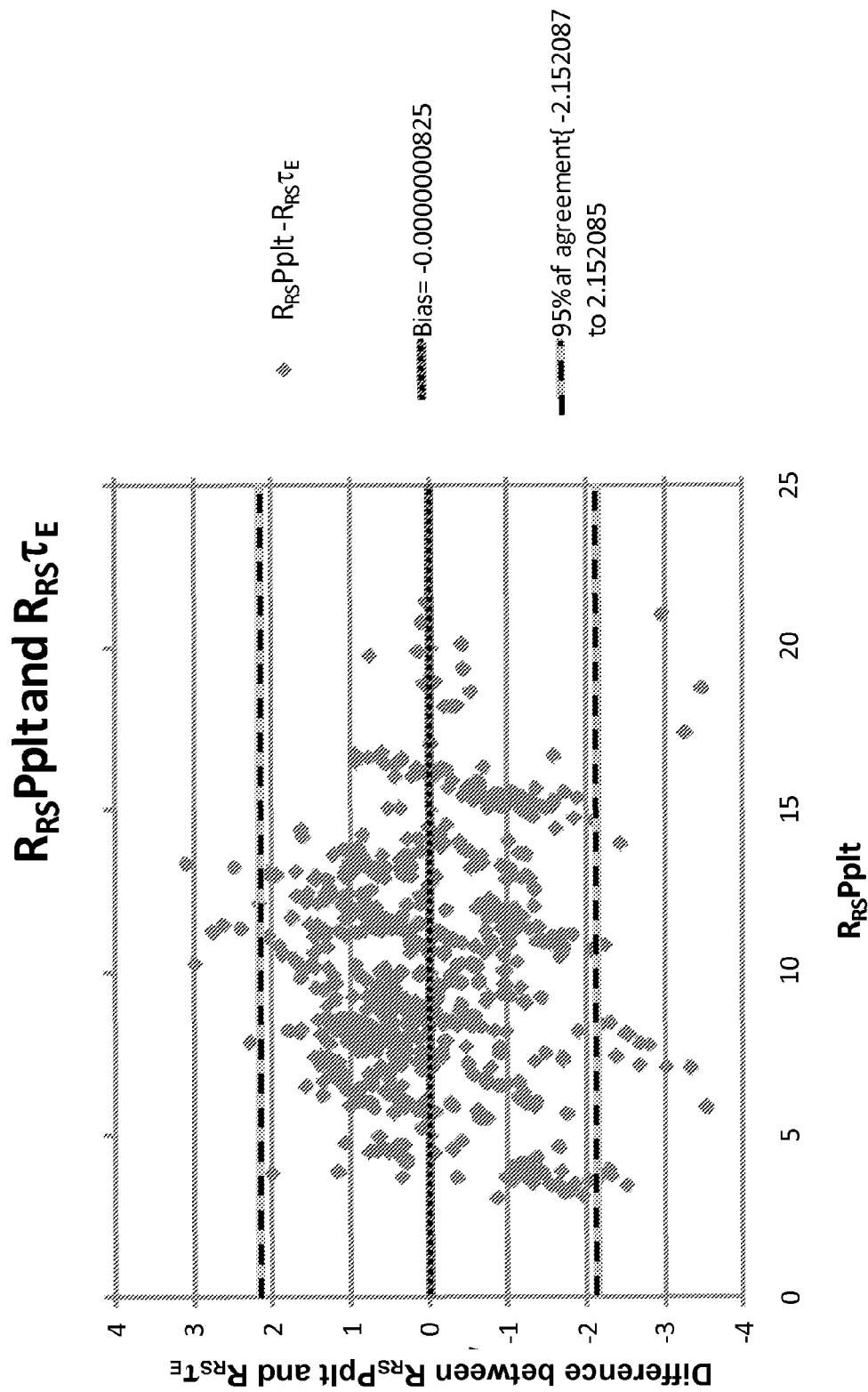
FIG. 8B is a Bland-Altman graph showing the difference between $R_{RS} P_{plt}$ and $R_{RS}\tau_E$, bias is essentially zero and precision of measurement is excellent.
Figure 8C:
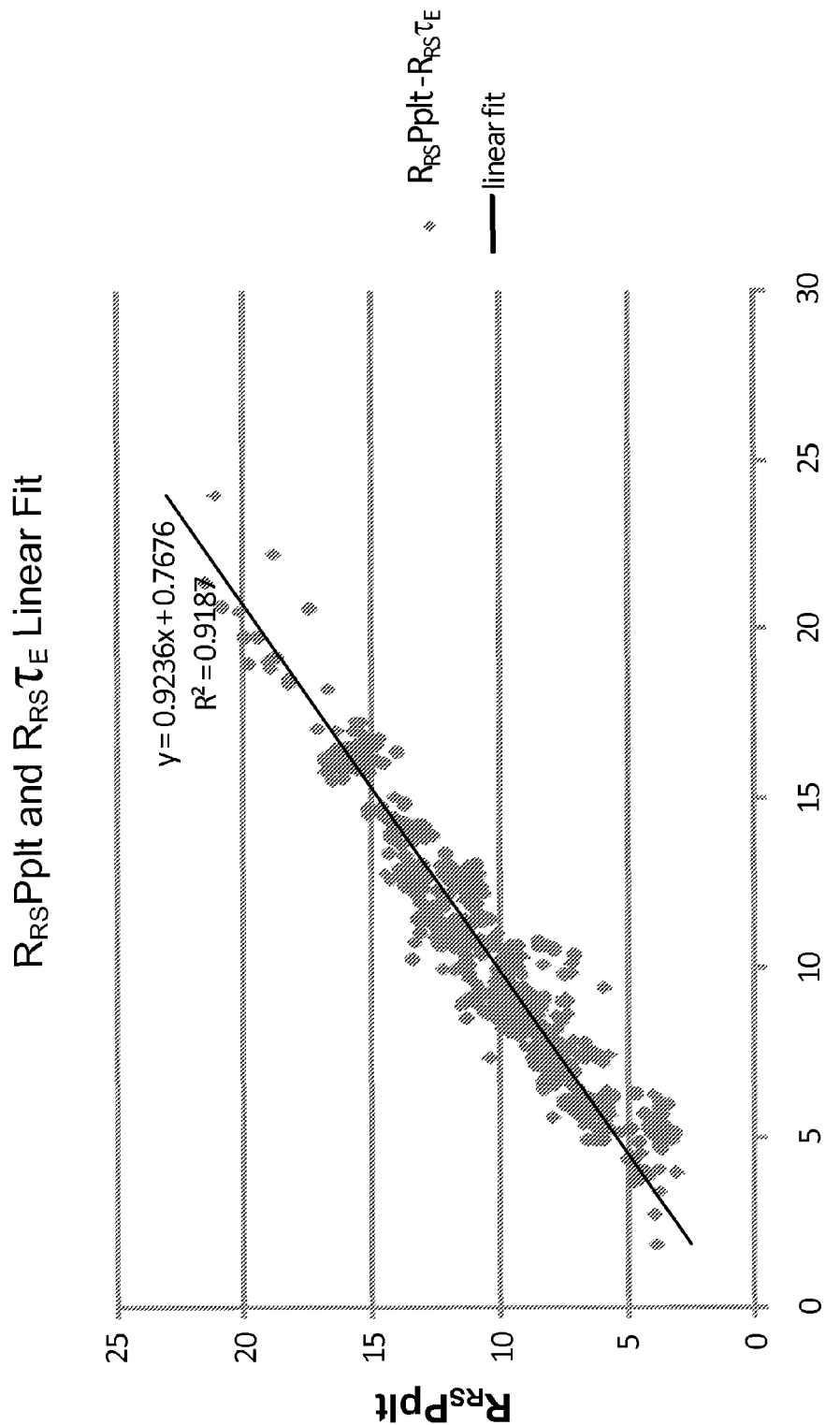
FIG. 8C is a linear fit graph between $R_{RS} P_{plt}$ and $R_{RS}\tau_E$.

Analysis of $R_{RS}$ calculation:

FIG. 8A is a graphical illustration of a regression analysis between calculated $R_{RS}$ from $\tau_E$ compared with the standard calculated $R_{RS}$ from $P_{plt}$, where $r^2$=0.918. FIG. 8B illustrates a Bland-Altman graph of the difference between $R_{RS}P_{plt}$ and $R_{RS}\tau_E$, where Bias=0.00000008, 95% limit of agreement={-2.15 to 2.15}. FIG. 8C is a linear fit graph between $R_{RS}P_{plt}$ and $R_{RS}\tau_E$, where Proportional=0.923.

EXAMPLE 2

Continuous and accurate estimates of $P_{plt}$ and $C_{RS}$ using the $\tau_E$ from passive deflation of the lungs during PSV, without the need for IMV with EIP, were validated using a population of twenty-four (24) adult patients in respiratory failure requiring mechanical ventilation and receiving PSV.

The 24 adults consisted of 10 males and 14 females with ranges in age 56.1±16.6 yrs and weight 79.9±28.8 kg. They had heterogeneous causes of respiratory failure and were breathing spontaneously with PSV. PSV ranged between 5 and 20 cm $H_2O$. Applying the same tidal volume, PSV and IMV with EIP were compared in the same patients. During PSV, $P_{plt}$ and $C_{RS}$ were obtained by integrating the $\tau_E$ from the expiratory volume and flow waveforms. During IMV and EIP, $P_{plt}$ was obtained from viewing pressure plateau of the airway pressure waveform at EIP. Data were analyzed using regression and Bland-Altman analysis; alpha was set at 0.05.

Figure 11:
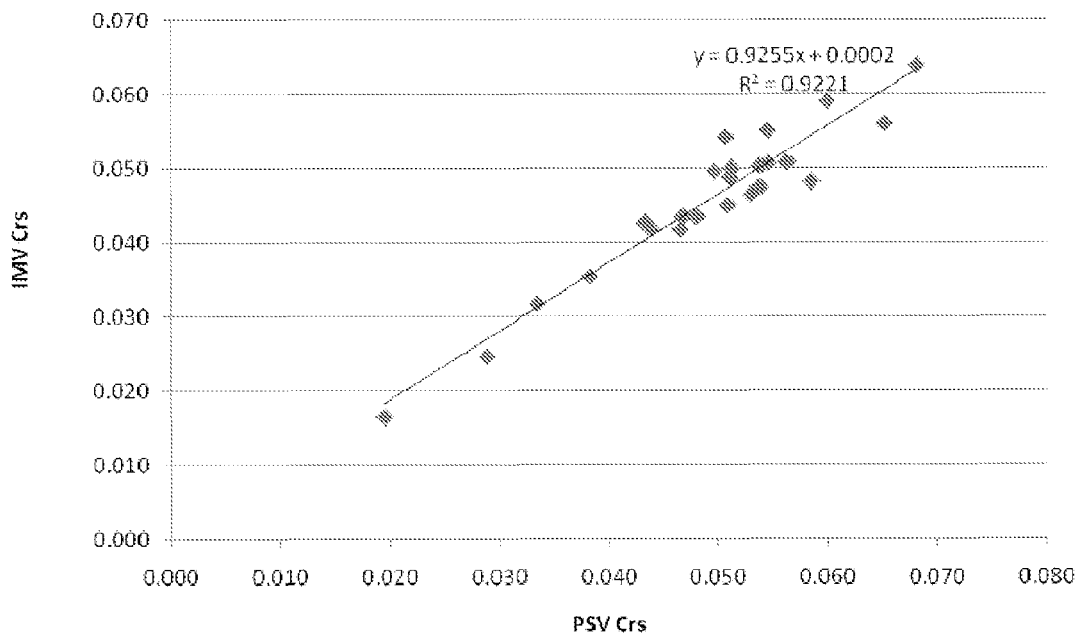
FIG. 11 is a linear fit graph between PSV $P_{plt}$ and IMV $P_{plt}$.
Figure 12:
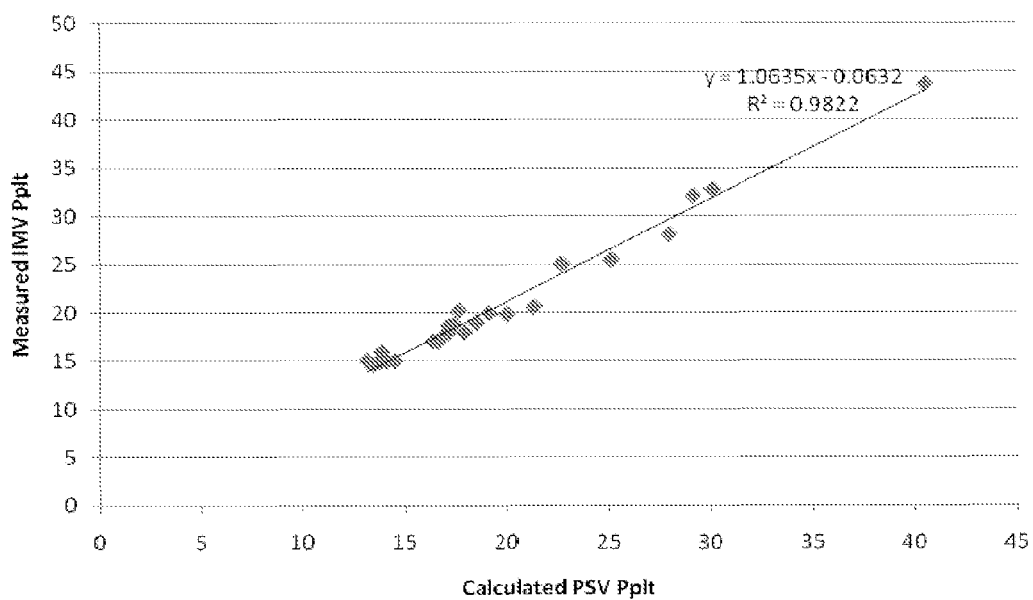
FIG. 12 is a linear fit graph between PSV $C_{RS}$ and IMV $C_{RS}$.

During PSV, $P_{plt}$ and $C_{RS}$ from the $\tau_E$ method were 19.65±6.6 cm $H_2O$ and 0.051±0.0124 ml/cm $H_2O$, respectively. During IMV with EIP, $P_{plt}$ and $C_{RS}$ were 20.84±7.17 cm $H_2O$ and 0.046±0.011 ml/cm $H_2O$, respectively (no significant differences in all measurements). Comparing both measuring methods, the relationships between $P_{plt}$ and $C_{RS}$ were $r^2$=0.98 (FIG. 11) and $r^2$=0.92 (FIG. 12), respectively (p<0.05)). Bland-Altman plots for $P_{plt}$ and $C_{RS}$ showed bias at 1.17 and -0.0035, respectively and precision at ±1 and ±0.0031, respectively.

It should be understood that the example and embodiments described herein are for illustrative purposes only and that various modifications or changes in light thereof will be suggested to persons skilled in the art and are to be included within the spirit and purview of this application and the scope thereof.

All patents, patent applications, provisional applications, and publications referred to or cited herein are incorporated by reference in their entirety, including all figures and tables, to the extent they are not inconsistent with the explicit teachings of this specification.

We claim:

1. A method for real time estimation of at least one selected from the group consisting of $C_{RS}$ (respiratory system compliance), $R_{RS}$ (patient airway resistance), and $P_{plt}$ inspiratory plateau pressure, comprising: (a) receiving respiratory parameters of a patient from a device that interfaces with patient pulmonary system and measures the respiratory parameters; (b) calculating, with a processor unit, the patient's $\tau_E$ (expiratory time constant) using at least one respiratory parameter from step (a), and (c) calculating with the processor unit at least one estimate selected from the group consisting of $C_{RS}$, $R_{RS}$, and $P_{plt}$, using at least one respiratory parameter from step (a) and the patient's $\tau_E$ from step (b), wherein the at least one respiratory parameter used to calculate the patient's $\tau_E$ is from exhalation and wherein the at least one respiratory parameter used to calculate at least one real time estimate selected from the group consisting of $C_{RS}$, $R_{RS}$, and $P_{plt}$, is from inspiration.

2. The method of claim 1, wherein the respiratory parameters include one or more from the group consisting of: inspiratory airway pressure, expiratory airway pressure, inspiratory flow rate expiratory flow rate, airway volume, airway resistance, expiratory carbon dioxide flow waveform, pulse oximeter plethysmogram waveforms, tidal volume, breathing frequency (f), peak inspiratory pressure (PIP), inspiratory time, $P_{0.1}$, inspiratory trigger time, and trigger depth.

3. The method of claim 1, wherein the respiratory parameter used to calculate at least one real time estimate selected from the group consisting of $C_{RS}$, $R_{RS}$, and $P_{plt}$, is from a single point on an inspiratory time waveform.

4. The method of claim 3, wherein the single point is taken during minimal patient effort.

5. The method of claim 3, wherein the single point is taken at or near the end of the breath.

6. The method of claim 1, wherein the respiratory parameter used to calculate the patient's $\tau_E$ is from an expiratory waveform.

7. The method of claim 6, wherein the respiratory parameter is from the middle of the expiratory waveform.

8. The method of claim 1, wherein the patient's $\tau_E$ is calculated from a median or average of multiple $\tau_E$ estimates calculated during exhalation.

9. The method of claim 8, wherein the multiple $\tau_E$ estimates calculated are during exhalation where flow rate lies between 95% and 20% of peak expiratory flow rate.

10. The method of claim 8, wherein the multiple $\tau_E$, estimates calculated are during exhalation where flow rate lies between 95% and 70% of peak expiratory flow rate.

11. The method of claim 8, wherein the multiple $\tau_E$ estimates calculated are during exhalation between 80% of exhaled volume and 20% of exhaled volume.

12. The method of claim 1, further comprising the step of applying a correction factor to the patient's $\tau_E$ that is calculated from exhalation, wherein the correction factor is derived from any one or more of the following: peak inspiratory flow, peak expiratory flow, and the equation $\tau_E(t)=\tau_E\text{total}(t)-(\text{Rvent}(t)*C_{est})$.

13. The method of claim 1, wherein the calculated estimates of $P_{plt}$, $C_{RS}$, or $R_{RS}$ are used in any one or more of the following functions: estimating patient effort of breathing, estimating patient resistance, estimating patient compliance, diagnosing pulmonary condition or disease, assessing efficacy of ventilation intervention, establishing ventilator settings for patient treatment, assessing efficacy of pharmaceutical therapy, assessing patient pulmonary mechanics during application of pharmaceuticals, identifying obstructions or obstacles affecting patient ventilation, determining and/or optimizing patient synchrony, optimizing ventilator on-triggering and off-triggering, assessing overall patient health, and assessing overall patient response to treatment.

14. The method of claim 1, wherein 0 to 0.1 seconds of the exhalation is excluded from the at least one respiratory parameter used to calculate the patient's $\tau_E$.

15. The method of claim 1, wherein the exhalation beyond 0.5 seconds of exhalation is excluded from the at least one respiratory parameter used to calculate the patient's $\tau_E$.

16. The method of claim 3, wherein the single point on the inspiratory time waveform used to calculate at least one estimate selected from the group consisting of $C_{RS}$, $R_{RS}$, and $P_{plt}$ is the last point of inhalation wherein the patient is exerting least effort.

17. The method of claim 8, wherein the median of multiple $\tau_E$ estimates is calculated during exhalation where flow is less than 80% of peak inspiratory flow but greater than 0.1 liters per second (LPS).

18. The method of claim 7, wherein the respiratory parameter is from the middle of the expiratory waveform from 0.1 seconds to 0.5 seconds after the beginning of exhalation.

* * * * *

UNITED STATES PATENT AND TRADEMARK OFFICE
CERTIFICATE OF CORRECTION

PATENT NO. : 8,728,002 B2
APPLICATION NO. : 13/260467
DATED : May 20, 2014
INVENTOR(S) : Nawar Nazar Yousif Al-Rawas et al.

Page 1 of 2

It is certified that error appears in the above-identified patent and that said Letters Patent is hereby corrected as shown below:

In the Specification

Column 1,
Line 36, "and $_{RRS}$" should read --and $R_{RS}$- --.

Column 1,
Line 59, "dve an" should read --give an--.

Column 5,
Line 38-39, "$P_{plt}(\tau_F)$ versus measured Pplt," should read --$P_{plt}(\tau_E)$ versus measured Pplt--.

Column 5,
Line 41, "$P_{ply}$," should read --$P_{plt}$,--.

Column 6,
Line 67, "$\dot{V}_{exh}(t)$," should read -- $\dot{V}_{exh}(t))$ --.

Column 8,
Line 46, "(R vent (t) $C_{est}$)" should read --(R vent (t) * $C_{est}$)--.

Column 8,
Line 57, "$\dot{V}_{inj}$" should read -- $\dot{V}_{inh}$ --.

Column 9,
Line 2, "$\dot{V}_{inh}$ inspiratory" should read -- $\dot{V}_{inh}$ is inspiratory --.

Column 9,
Line 6, "$C_{RS} R_{RS}$" should read --$C_{RS} + R_{RS}$--.

Signed and Sealed this
Eleventh Day of November, 2014

Michelle K. Lee
*Deputy Director of the United States Patent and Trademark Office*

Column 9,
Line 23, "C$_{Rs}$" should read --C$_{RS}$--.

Column 9,
Line 28, "$P_{pit} = \frac{V_T \times P_{aw} - V_T \times PEEP}{(V_T + \tau_E * V_{inh}) + PEEP}$" should read --$P_{plt} = \frac{V_T \times P_{aw} - V_T \times PEEP}{(V_T + \tau_E * \dot{V}_{inh})} + PEEP$--.

Column 10,
Line 66, "(NIPPY)" should read --(NIPPV)--.

Column 14,
Line 6, "P$_{ply}$" should read --P$_{plt}$--.

In the Claims

Column 15,
Line 31, Claim 2, "rate expiratory flow" should read --rate, expiratory flow--.

Column 16,
Line 7, Claim 10, "$\tau_E$, estimates" should read --$\tau_E$ estimates--.

Column 16,
Line 39-40, Claim 16, "P$_{plt}$ is" should read --P$_{plt}$, is--.